United States Patent [19]

Shiokawa et al.

[11] Patent Number: 5,066,680
[45] Date of Patent: Nov. 19, 1991

[54] SUBSTITUTED-ACETAMIDE COMPOUND AND A PROCESS FOR THE PREPARATION THEREOF

[75] Inventors: Youichi Shiokawa, Ibaraki; Kazuo Okumura; Kazuhiko Take, both of Osaka; Kazunori Tsubaki, Ikeda, all of Japan

[73] Assignee: Fujisawa Pharmaceutical Co., Ltd., Osaka, Japan

[21] Appl. No.: 475,301

[22] Filed: Feb. 5, 1990

[30] Foreign Application Priority Data

Feb. 14, 1989 [GB] United Kingdom .................. 8903253
Apr. 28, 1989 [GB] United Kingdom .................. 8909796

[51] Int. Cl.$^5$ .......................................... A61K 31/165
[52] U.S. Cl. .................................. 514/622; 514/214; 514/238.2; 514/255; 514/331; 514/357; 514/399; 514/454; 514/539; 514/542; 514/617; 514/620; 514/621; 540/585; 544/168; 544/397; 546/221; 546/234; 546/337; 548/343; 549/388; 560/39; 564/164; 564/169; 564/170; 564/174; 564/181

[58] Field of Search ................. 564/171, 174; 514/622

[56] References Cited

U.S. PATENT DOCUMENTS

| 2,009,144 | 7/1935 | Miescher et al. | 564/171 |
|---|---|---|---|
| 2,733,256 | 1/1956 | Krapcho et al. | 564/171 |
| 2,862,965 | 12/1958 | Lott et al. | 564/171 |
| 2,932,645 | 4/1960 | Sumerford et al. | 564/171 |
| 3,446,811 | 5/1969 | Nordin et al. | 564/171 |
| 3,594,401 | 7/1971 | Cavalla et al. | 564/171 |
| 4,518,789 | 5/1985 | Yu et al. | 514/544 |

FOREIGN PATENT DOCUMENTS 658183 2/1963 Canada .................. 564/171

*Primary Examiner*—Glennon H. Hollrah
*Assistant Examiner*—Scott C. Rand
*Attorney, Agent, or Firm*—Oblon, Spivak, McClelland, Maier & Neustadt

[57] ABSTRACT

Compounds of the formula

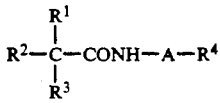

wherein
$R^1$ is aryl which may have one or more suitable substituent(s),
$R^2$ is aryl which may have one or more suitable substituent(s), lower alkyl or cyclo(lower)alkyl,
$R^3$ is hydrogen, hydroxy, halogen, lower alkenyl, amino or protected amino,
$R^4$ is a group of the formula:

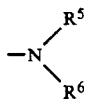

wherein
$R^5$ is lower alkyl which may have one or more suitable substituent(s), cyclo(lower)alkyl, aryl, ar(lower)alkyl which may have one or more suitable substituent(s), and
$R^6$ is hydrogen or lower alkyl; or N-containing heterocyclic group which may have one or more suitable substituent(s), and
A is lower alkylene or lower alkynylene, in which $R^1$ and $R^2$ may be linked through oxygen atom, their preparation and use in treatment of dysuria, and starting materials for their preparation.

9 Claims, No Drawings

SUBSTITUTED-ACETAMIDE COMPOUND AND A PROCESS FOR THE PREPARATION THEREOF

This invention relates to a novel substituted-acetamide compound and a pharmaceutically acceptable salt thereof.

More particularly, it relates to a novel substituted-acetamide compound and a pharmaceutically acceptable salt thereof which have anticholinergic activity, and are useful for the treatment of dysuria such as pollakiuria, urinary incontinence or the like in case of nervous pollakiuria, neurogenic bladder dysfunction, nocturia, unstable bladder, cystospasm, chronic cystitis, chronic prostatitis or the like; and for the treatment of convulsion and/or hypanakinesis in case of gastric ulcer, duodenal ulcer, gastroxynsis, esophagospasm, gastritis, enteritis, irritable colon syndrome, enteralgia, cholecystitis, cholangitis, pylorospasm, pancreatitis, pain in case of pancreatitis, biliary dyskinesia, aftereffect after cholecystectomy, urinary calculus, cystitis, dysmenorrhea, hidrosis, convulsion of urinary tract; and which are expected to be useful for the treatment of asthma, Parkinson disease, angina pectris or the like; to a process for the preparation thereof, to a pharmaceutical composition comprising the same and to a method for the treatment of aforesaid diseases in human being or animals.

One object of this invention is to provide a novel substituted-acetamide compound and a pharmaceutically acceptable salt thereof which are useful for the treatment of aforesaid diseases.

Another object of this invention is to provide a process for the preparation of said substituted-acetamide compound or a salt thereof.

A further object of this invention is to provide a pharmaceutical composition comprising, as an active ingredient, said substituted-acetamide compound or a pharmaceutically acceptable salt thereof, which is useful as an agent for the treatment of aforesaid diseases.

Still further object of this invention is to provide a therapeutical method for the treatment of aforesaid diseases.

The object substituted-acetamide compound of this invention is novel and can be represented by the following formula (I):

$$R^2-\underset{\underset{R^3}{|}}{\overset{\overset{R^1}{|}}{C}}-CONH-A-R^4 \quad (I)$$

wherein
R$^1$ is aryl which may have one or more suitable substituent(s),
R$^2$ is aryl which may have one or more suitable substituent(s), lower alkyl or cyclo(lower)alkyl,
R$^3$ is hydrogen, hydroxy, halogen, lower alkenyl, amino or protected amino,
R$^4$ is a group of the formula:

wherein
R$^5$ is lower alkyl which may have one or more suitable substituent(s), cyclo(lower)alkyl, aryl, ar(lower)alkyl which may have one or more suitable substituent(s), and
R$^6$ is hydrogen or lower alkyl; or N-containing heterocyclic group which may have one or more suitable substituent(s), and
A is lower alkylene or lower alkynylene, in which R$^1$ and R$^2$ may be linked through oxygen atom.

In the object compound (I), there is a stereo isomer due to the existence of asymmetric carbon atom. Said stereo isomer is also included within the scope of this invention.

The object compound (I) or a salt thereof can be prepared by the processes as illustrated in the following reaction schemes.

Process 1

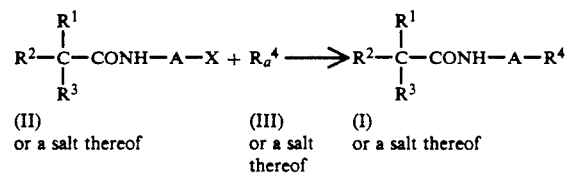

(II)     (III)     (I)
or a salt thereof     or a salt thereof     or a salt thereof Process 2

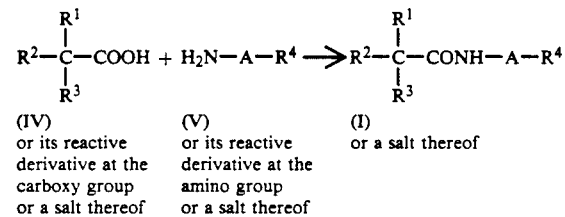

(IV)     (V)     (I)
or its reactive derivative at the carboxy group or a salt thereof     or its reactive derivative at the amino group or a salt thereof     or a salt thereof Process 3

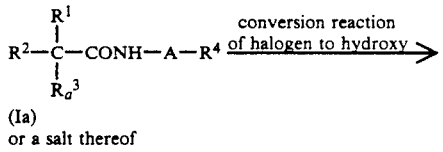

(Ia)
or a salt thereof

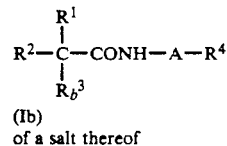

(Ib)
of a salt thereof

Process 4

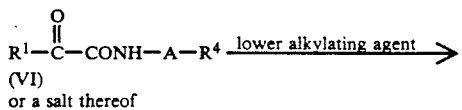

(VI)
or a salt thereof

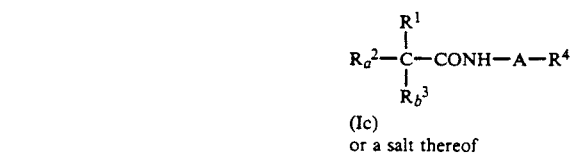

(Ic)
or a salt thereof

Process 5

-continued

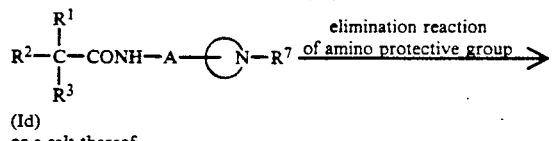

(Id)
or a salt thereof

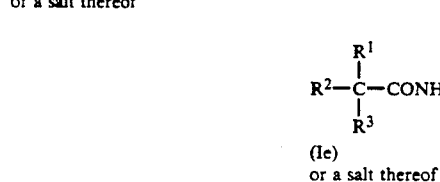

(Ie)
or a salt thereof

Process 6

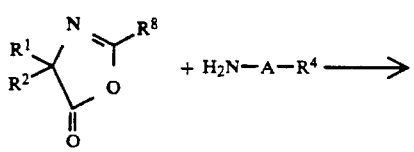

(VII)
or a salt thereof (V)
or its reactive derivative at the
amino group or a salt thereof

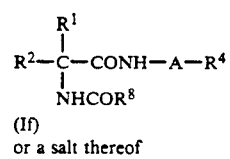

(If)
or a salt thereof

Process 7

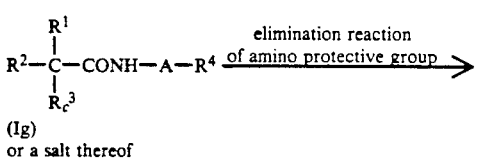

(Ig)
or a salt thereof $$R^2-\underset{R_d^3}{\underset{|}{\overset{R^1}{\overset{|}{C}}}}-CONH-A-R^4$$

(Ih)
or a salt thereof wherein
R$^1$, R$^2$, R$^3$, R$^4$ and A are each as defined above,
R$_a^2$ is lower alkyl,
R$_a^3$ is halogen,
R$_b^3$ is hydroxy,
R$_c^3$ is protected amino,
R$_d^3$ is amino,
R$_d^4$ is a compound of the formula:

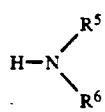

wherein R$^5$ and R$^6$ are each as defined above; or N-containing heterocyclic compound which may have one or more suitable substituent(s),
R$^7$ is amino protective group,
R$^8$ is lower alkyl which may have one or more halogen,
a group of the formula:

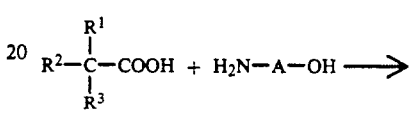

is N-containing heterocyclic group which may have one or more suitable substituent(s), and
X is a leaving group.
The starting compound (I) or a salt thereof is novel and can be prepared by the processes as shown below.

Process A $$R^2-\underset{R^3}{\underset{|}{\overset{R^1}{\overset{|}{C}}}}-COOH + H_2N-A-OH \longrightarrow$$

(IV)
or its reactive
derivative at
the carboxy group
or a salt thereof (VIII)
or its reactive
derivative at
the amino group
or a salt thereof

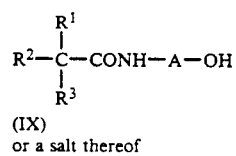

(IX)
or a salt thereof

Process B

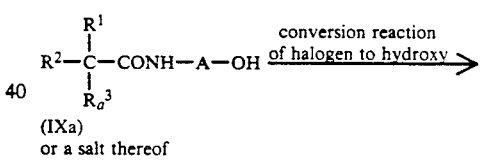

(IXa)
or a salt thereof

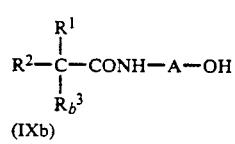

(IXb)
or a salt thereof

Process C

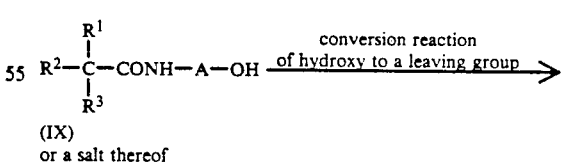

(IX)
or a salt thereof

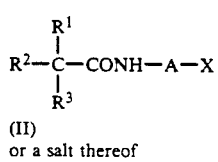

(II)
or a salt thereof

Process D

-continued

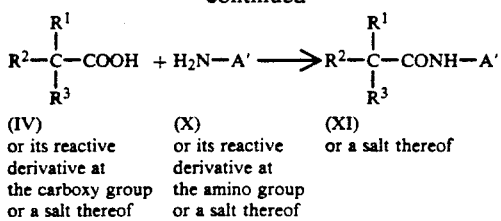

(IV)
or its reactive
derivative at
the carboxy group
or a salt thereof (X)
or its reactive
derivative at
the amino group
or a salt thereof (XI)
or a salt thereof Process E

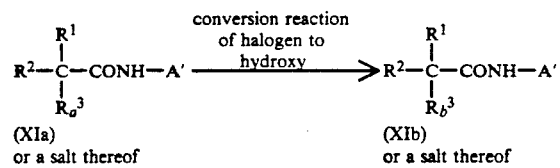

(XIa)
or a salt thereof (XIb)
or a salt thereof

Process F

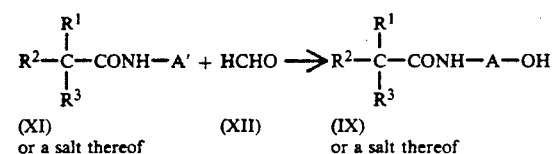

(XI)
or a salt thereof (XII)

(IX)
or a salt thereof wherein $R^1$, $R^2$, $R^3$, $R_a^3$, $R_b^3$, A and X are each as defined above, and A' is ω-lower alkynyl.

Some of the compound (V) are novel, and can be prepared according to the methods disclosed in Preparations described later or similar manners thereto.

Suitable pharmaceutically acceptable salts of the object compound (I) are conventional non-toxic mono or di salts and include an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, hydroiodide, sulfate, phosphate, etc.], a salt with an amino acid [e.g. arginine salt, aspartic acid salt, glutamic acid salt, etc.], and the like.

In the above and subsequent descriptions of this specification, suitable examples of the various definitions are explained in detail as follows:

The term "lower" is intended to mean 1 to 6 carbon atom(s), unless otherwise indicated.

Suitable "aryl" may include phenyl, naphthyl, pentalenyl, anthracenyl and the like, in which the preferred one may be phenyl.

Said "aryl" may have one or more (preferably 1 to 3) suitable substituent(s) such as halogen (e.g. fluoro, chloro, bromo, iodo), lower alkyl (e.g. methyl, ethyl, propyl, isopropyl, butyl, t-butyl, pentyl, hexyl, etc.), lower alkoxy (e.g. methoxy, ethoxy, propoxy, isopropoxy, butoxy, t-butoxy, pentyloxy, hexyloxy, etc.) or the like.

Preferred "aryl having one or more suitable substituent(s)" may be phenyl having 1 suitable substituent selected from a group consisting of halogen, lower alkyl and lower alkoxy, the more preferred one may be phenyl having halogen, phenyl having $(C_1-C_4)$alkyl and phenyl having $(C_1-C_4)$alkoxy, and the most preferred one may be phenyl having chloro, phenyl having methyl and phenyl having methoxy.

Suitable "ar(lower)alkyl" may include benzyl, benzhydryl, trityl, 1-phenylethyl, 2-phenylethyl, 2-benzhydrylethyl, 3-phenylpropyl, 1-methyl-2-phenylethyl, 1-phenylbutyl, 4-tritylbutyl, 1,1-dimethyl-2-phenylethyl, 4-phenylpentyl, 6-phenylhexyl and the like, in which the more preferred one may be phenyl$(C_1-C_4)$alkyl and the most preferred one may be benzyl, 2-phenylethyl and 1-methyl-2-phenylethyl.

Said "ar(lower)alkyl" may have one or more (preferably 1 to 3) suitable substituent(s) such as lower alkoxy (e.g. methoxy, ethoxy, propoxy, isopropoxy, butoxy, t-butoxy, pentyloxy, hexyloxy, etc.) or the like, in which the preferred one may be methoxy.

Suitable "cyclo(lower)alkyl" may include the ones having 3 to 8 carbon atoms such as cyclopropyl, cyclobutyl, cyclopentyl, cyclohexyl, cycloheptyl and cyclooctyl, in which the preferred one may be cyclo$(C_3-C_7)$alkyl and the more preferred one may be cyclopropyl, cyclopentyl, cyclohexyl and cycloheptyl.

Suitable "halogen" may be fluoro, chloro, bromo and iodo, in which the preferred one may be chloro.

Suitable "lower alkyl" may include the straight and branched ones such as methyl, ethyl, propyl, isopropyl, butyl, t-butyl, pentyl, hexyl or the like, in which the preferred one may be $(C_1-C_4)$alkyl and the more preferred one may be methyl, ethyl, propyl, butyl and t-butyl.

Suitable "lower alkenyl" may include the straight and branched ones such as vinyl, allyl, 2-methyl-2-propenyl, 2-butenyl, 1-pentenyl, 5-hexenyl or the like, in which the preferred one may be $(C_2-C_4)$alkenyl and the more preferred one may be allyl.

Suitable "ω-lower alkynyl" may include the straight and branched ones in which the triple bond exists at the terminal carbon atom such as ethynyl, 2-propynyl, 3-butynyl, 1-methyl-2-propynyl, 4-pentynyl, 5-hexynyl or the like, in which the preferred one may be ω-$(C_2-C_4)$alkynyl and the more preferred one may be 2-propynyl.

Suitable "lower alkyl" in "lower alkyl which may have one or more suitable substituent(s)" may be the ones as exemplified before for "lower alkyl".

Suitable examples of "suitable substituent(s)" in "lower alkyl which may have one or more suitable substituent(s)" may include hydroxy, protected carboxy, and the like.

Suitable "protected carboxy" may be conventionally esterified carboxy such as lower alkoxycarbonyl (e.g. methoxycarbonyl, ethoxycarbonyl, propoxycarbonyl, butoxycarbonyl, t-butoxycarbonyl, pentyloxycarbonyl, hexyloxycarbonyl, etc.) or the like, in which the preferred one may be $(C_1-C_4)$alkoxycarbonyl and the more preferred one may be ethoxycarbonyl.

The preferred "lower alkyl having one or more suitable substituent(s)" may be lower alkyl having 1 to 3 suitable substituent(s) selected from a group consisting of hydroxy or lower alkoxycarbonyl, the more preferred one may be hydroxy(lower)alkyl [e.g. hydroxymethyl, 2-hydroxyethyl, 2-hydroxypropyl, 1-hydroxymethylethyl, 3-hydroxybutyl, 1-hydroxymethyl-1-methylethyl, 5-hydroxypentyl, 2-hydroxyhexyl, etc.) and lower alkoxycarbonyl(lower)alkyl (e.g. methoxycarbonylmethyl, ethoxycarbonylmethyl, 2-ethoxycarbonylethyl, 2-ethoxycarbonylpropyl, 1-propoxycarbonylmethylethyl, 3-t-butoxycarbonylbutyl, 1-butoxycarbonylmethyl-1-methylethyl, 5-pentyloxycarbonylpentyl, 2-hexyloxycarbonylhexyl, etc.), the much more preferred one may be hydroxy$(C_1-C_4)$alkyl and $(C_1-C_4)$alkoxycarbonyl(C $(C_1-C_4)$alkyl, and the most preferred one may be 2-hydroxyethyl and ethoxycarbonylmethyl.

Suitable "lower alkylene" may include the straight and branched ones such as methylene, ethylene, trimethylene, tetramethylene, 1,1-dimethylethylene, pentamethylene, hexamethylene, or the like, in which the preferred one may be ($C_1$-$C_4$)alkylene and the more preferred one may be methylene and ethylene.

Suitable "lower alkynylene" may include the straight and branched ones having 2 to 6 carbon atoms such as ethynylene, propynylene, 1-butynylene, 2-butynylene, 3-methyl-1-propynylene, 3,3-dimethyl-1-propynylene, 2-hexynylene, 3,4-dimethyl-1-butynylene or the like, in which the preferred one may be ($C_1$-$C_4$)alkynylene, and the more preferred one may be 2-butynylene.

Suitable "N-containing heterocyclic group" may include saturated or unsaturated, monocyclic or polycyclic heterocyclic group such as unsaturated 3 to 8-membered(more preferably 5 to 7-membered)heteromonocyclic group containing 1 to 4 nitrogen atom(s), for example, azepinyl (e.g. 1H-azepinyl, etc.), pyrrolyl, pyrrolinyl, imidazolyl, pyrazolyl, pyridyl and its N-oxide, dihydropyridyl, tetrahydropyridyl (e.g. 1,2,3,4-tetrahydropyridyl, 1,2,3,6-tetrahydropyridyl, etc.), pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.) etc.;

saturated 3 to 8-membered(more preferably 5 to 7 membered) heteromonocyclic group(containing 1 to 4 nitrogen atom(s), for example, perhydroazepinyl (e.g. perhydro-1H-azepinyl, etc.) pyrrolidinyl, imidazolidinyl, pyrazolidinyl, perhydrothiazolyl, perhydroisoxazolyl, piperidyl, piperazinyl, perhydropyrimidinyl, perhydropyridazinyl, morpholinyl, etc.;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;

saturated condensed heterocyclic group containing 1 to 4 nitrogen atom(s), for example, 7-azabicyclo[2.2.1]-heptyl, 3-azabicyclo[3.2.2]nonanyl, 1,5-diazabicyclo[4.3.0]nonanyl, perhydroindolyl, perhydroquinolyl, perhydrophthalazinyl, 6-oxa-3-azabicyclo[3.2.2]nonanyl, 1-thia-5-azabicyclo[4.3.0]nonanyl, etc.;

unsaturated 3 to 8-membered(more preferably 5 or 6-membered)heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.), etc.;

saturated 3 to 8-membered(more preferably 5 or 6-membered)heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered(more preferably 5 or 6-membered)heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered(more preferably 5 or 6-membered)heteromonocyclic group containing 1 to 2 sulfur atom(s) and 1 to 3 nitrogen atom(s), for example, thiazolidinyl, etc.;

unsaturated condensed heterocyclic group containing 1 to 2 sulfur atom(s) and 1 to 3 nitrogen atom(s), for example, benzothiazolyl, benzothiadiazolyl, etc.; in which the preferred one may include saturated 3 to 8 membered heteromonocyclic group containing 1 to 4 nitrogen atom(s), saturated condensed heterocyclic group containing 1 to 4 nitrogen atom(s), and saturated 3 to 8 membered heteromonocyclic group containing 1 to 2 oxygen atom(s) and 1 to 3 nitrogen atom(s).

Said "N-containing heterocyclic group" may have one or more (preferably 1 to 3) suitable substituent(s) such as aforesaid lower alkyl; hydroxy; aforesaid hydroxy(lower)alkyl; amino protective group such as mono-(or di- or tri-)phenyl(lower)alkyl (e.g. benzyl, benzhydryl, trityl, etc.), lower alkanoyl (e.g. formyl, acetyl, propionyl, butyryl, pivaloyl, hexanoyl, etc.) or the like; cyanoimino; or the like.

In "N-containing heterocyclic group which may have one or more suitable substituent(s)", the preferred one may be pyridyl, tetrahydropyridyl, imidazolidinyl, piperidyl, piperazinyl, morpholinyl and 3-azabicyclo[3.2.2]nonanyl, each of which may have lower alkyl, hydroxy, hydroxy(lower)alkyl, amino protective group or cyanoimino, the more preferred one may be pyridyl, 1,2,3,6-tetrahydropyridyl which may have lower alkyl or phenyl(lower)alkyl, imidazolidinyl which may have cyanoimino, piperidyl which may have lower alkyl, hydroxy or hydroxy(lower)alkyl, piperazinyl which may have lower alkyl, morpholinyl and 3-azabicyclo[3.2.2]nonanyl, and the most preferred one may be pyridyl, 1,2,3,6-tetrahydropyridin-4-yl, 1-methyl-1,2,3,6-tetrahydropyridin-4-yl, 1-ethyl-1,2,3,6-tetrahydropyridin-4-yl, 1-benzyl-1,2,3,6-tetrahydropyridin-4-yl, 2-cyanoimino-1-imidazolidinyl, piperidino, 1-ethyl-4-piperidyl, 4-hydroxypiperidino, 2-hydroxymethylpiperidino, 4-methyl-1-piperazinyl, morpholino and 3-azabicyclo[3.2.2]nonan-3-yl.

Suitable "N-containing heterocyclic compound which may have one or more suitable substituent(s)" may be the corresponding compound to aforesaid "N-containing heterocyclic group which may have one or more suitable substituent(s)".

Suitable "protected amino" may include acylamino, and the like.

Suitable examples of said "acylamino" may include lower alkanoylamino (e.g. formylamino, acetylamino, propionylamino, butyrylamino, isobutyrylamino, pivaloylamino, hexanoylamino, etc.), lower alkoxycarbonylamino (e.g. methoxycarbonylamino, ethoxycarbonylamino, propoxycarbonylamino, t-butoxycarbonylamino, pentyloxycarbonylamino, hexyloxycarbonylamino, etc.), lower alkoxycarbonyl(lower)-alkanoylamino (e.g. methoxycarbonylacetylamino, ethoxycarbonylacetylamino, 2-(propoxycarbonyl)propionylamino, 4-(t-butoxycarbonyl)butyrylamino, 2-(butoxycarbonylmethyl)propionylamino, 2-methyl-2-(pentyloxycarbonylmethyl)propionylamino, 6-hexyloxycarbonylhexanoylamino, etc.), lower alkanesulfonylamino (e.g. methanesulfonylamino, ethanesulfonylamino, propanesulfonylamino, butanesulfonylamino, t-butanesulfonylamino, pentanesulfonylamino, hexanesulfonylamino, etc.) and the like, each of which may have one or more suitable substituent(s) such as halogen, or the like.

In "protected amino", the preferred one may be lower alkanoylamino which may have halogen, the more preferred one may be ($C_1$-$C_4$)alkanoylamino having fluoro and the most preferred one may be 2,2,2-trifluoroacetylamino.

Suitable "a leaving group" may be aforesaid halogen, acyloxy such as sulfonyloxy (e.g. mesyloxy, tosyloxy, etc.), lower alkanoyloxy (e.g. acetoxy, etc.) or the like; and the like.

Suitable example of the group in case $R^1$ and $R^2$ are linked through oxygen atom may include the case a group of the formula:

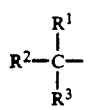

forms a group of the formula:

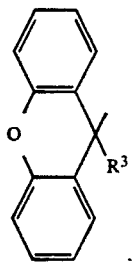

The processes for preparing the object compound (I) of this invention are explained in detail in the following.

PROCESS 1

The object compound (I) or a salt thereof can be prepared by reacting the compound (II) or a salt thereof with the compound (III) or a salt thereof.

Suitable salts of the compound (II) and (III) can be referred to the ones as exemplified for the compound (I).

The present reaction may be carried out in a solvent such as water, phosphate buffer, acetone, chloroform, acetonitrile, nitrobenzene, methylene chloride, ethylene chloride, formamide, N,N-dimethylformamide, methanol, ethanol, diethyl ether, dioxane, tetrahydrofuran, dimethyl sulfoxide, or any other organic solvent which does not adversely affect the reaction, preferably in ones having strong polarities. Among the solvents, hydrophilic solvents may be used in a mixture with water.

The reaction is preferably conducted in the presence of a base, for example, inorganic base such as alkali metal hydride (e.g. sodium hydride), alkali metal hydroxide, alkali metal carbonate, alkali metal bicarbonate, organic base such as trialkylamine, and the like.

The reaction temperature is not critical, and the reaction is usually carried out at room temperature, under warming or under heating.

The present reaction is preferably carried out in the presence of alkali metal halide [e.g. sodium iodide, potassium iodide, etc.], alkali metal thiocyanate [e.g. sodium thiocyanate, potassium thiocyanate, etc.] or the like.

PROCESS 2

The object compound (I) or a salt thereof can be prepared by reacting the compound (IV) or its reactive derivative at the carboxy group or a salt thereof with the compound (V) or its reactive derivative at the amino group or a salt thereof.

Suitable salt of the compound (IV) may include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt dicyclohexylamine salt, N,N-dibenzylethylenediamine salt, etc.], and the like.

Suitable salt of the compound (V) can be referred to the ones as exemplified for the compound (I).

Suitable reactive derivative at the carboxy group of the compound (IV) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g. cyanomethyl ester, methoxymethyl ester, dimethyliminomethyl [$(CH_3)_2N^{30}=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (IV) to be used.

Suitable reactive derivative at the amino group of the compound (V) may include Schiff's base type imino or its tautomeric enamine type isomer formed by the reaction of the compound (V) with a carbonyl compound such as aldehyde, ketone or the like; a silyl derivative formed by the reaction of the compound (V) with a silyl compound such as bis(trimethylsilyl)acetamide, mono(-trimethylsilyl)acetamide, bis(trimethylsilyl)urea or the like; a derivative formed by reaction of the compound (V) with phosphorus trichloride or phosgene, and the like.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine, benzene or any other organic solvent which does not adversely influence the reaction. These conventional solvent may also be used in a mixture with water.

In this reaction, when the compound (IV) is used in a free acid form or its salt form, the reaction is preferably carried out in the presence of a conventional condensing agent such as N,N'-dicyclohexylcarbodiimide; N- cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene, trialkyl phosphite; ethyl polyphosphate; isopropyl polyphosphate; phosphorus oxychloride (phosphoryl chloride); phosphorus trichloride; phosphorus pentachloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

PROCESS 3

The object compound (Ib) or a salt thereof can be prepared by subjecting the compound (Ia) or a salt thereof to conversion reaction of halogen to hydroxy.

Suitable salts of the compounds (Ia) and (Ib) can be referred to the ones as exemplified for the compound (I).

This conversion reaction can be carried out in a conventional hydrolysis condition.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]-non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid e.g. hydrochloric acid, hydrobromic acid, sulfuric acid, etc.].

The elimination using Lewis acid such as trihaloacetic acid [e.g. trichloroacetic acid, trifluoroacetic acid, etc.] or the like is preferably carried out in the presence of cation trapping agents e.g. anisole, phenol, etc.].

The reaction is usually carried out in a solvent such as water, an alcohol [e.g. methanol, ethanol, etc.], methylene chloride, tetrahydrofuran, dioxane, a mixture thereof or any other solvent which does not adversely influence the reaction. A liquid base or acid can be also used as the solvent.

The reaction temperature is not critical and the reaction is usually carried out under cooling to heating.

PROCESS 4

The object compound (Ic) or a salt thereof can be prepared by reacting the compound (VI) or a salt thereof with lower alkylating agent.

Suitable salts of the compounds (Ic) and (VI) can be referred to the ones as exemplified for the compound (I).

Suitable "lower alkylating agent" in this process may include metalated lower alkyl such as Grignard reagent of the formula:

$R_a^2$-Mg-Y (wherein $R_a^2$ is as defined above, and Y is aforesaid halogen), a compound of the formula:

$R_a^2$-Li (wherein $R_a^2$ is as defined above), or the like, and the like.

The present reaction may be carried out in a solvent such as diethyl ether, tetrahydrofuran, n-hexane or any other solvent which does not adversely influence the reaction.

The reaction temperature is not critical and the reaction is usually carried out under cooling to heating.

PROCESS 5

The object compound (Ie) or a salt thereof can be prepared by subjecting the compound (Id) or a salt thereof to elimination reaction of amino protective group.

Suitable salts of the compounds (Id) and (Ie) can be referred to the ones as exemplified for the compound (I).

This reaction is carried out in accordance with a conventional method such as hydrolysis, reduction, the reaction with haloformic acid ester or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate, or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Suitable "haloformic acid ester" used in the reaction with haloformic acid ester may include methyl chloroformate, ethyl chloroformate, 1-chloroethyl chloroformate, p-nitrophenyl chloroformate and the like.

The reaction is usually carried out in a solvent such as methylene chloride, chloroform, benzene or any other solvent which does not adversely influence the reaction.

The reaction temperature is not critical and the reaction is usually carried out under warming to heating.

PROCESS 6

The object compound If) or a salt thereof can be prepared by reacting the compound (VII) or a salt thereof with the compound (V) or its reactive derivative at the amino group or a salt thereof.

Suitable salt of the compound (VII) can be referred to the ones as exemplified for the compound (I).

This reaction can be carried out in a similar manner to that of Process 2 mentioned in the above, and therefore the reaction mode and reaction conditions [e.g. base, catalyst, reactive derivative, solvent, reaction temperature, etc.] of this reaction are to be referred to those as explained in Process 2.

PROCESS 7

The object compound (Ih) or a salt thereof can be prepared by subjecting the compound (Ig) or a salt thereof to elimination reaction of amino protective group.

Suitable salts of the compounds (Ig) and (Ih) can be referred to the ones as exemplified for the compound (I).

This reaction can be carried out in a similar manner to that of Process 5 mentioned in the above, and therefore the reaction mode and reaction conditions of this reaction are to be referred to those as explained in Process 5.

When the object compound (I) obtained by aforesaid processes is in free form, it can h=converted to its salt according to a conventional manner.

In the following, the processes for preparing the starting compound (II) are explained in detail.

PROCESS A

The compound (IX) or a salt thereof can be prepared by reacting the compound (IV) or its reactive derivative at the carboxy group or a salt thereof with the compound (VIII) or its reactive derivative at the amino group or a salt thereof.

Suitable salt of the compound (VIII) can be referred to the ones as exemplified for the compound (I).

This reaction can be carried out in a similar manner to that of Process 2 mentioned in the above, and therefore the reaction mode and reaction conditions [e.g. base, catalyst, reactive derivative, solvent, reaction temperature, etc.] of this reaction are to be referred to those as explained in Process 2.

PROCESS B

The compound (IXb) or a salt thereof can be prepared by subjecting the compound (IXa) or a salt thereof to conversion reaction of halogen to hydroxy.

Suitable salts of the compounds (IXa) and (IXb) can be referred to the ones as exemplified for the compound (I).

This reaction can be carried out in a similar manner to that of Process 3 mentioned in the above, and therefore the reaction mode and reaction conditions of this reaction are to be referred to those as explained in Process 3.

PROCESS C

The compound (II or a salt thereof can be prepared by subjecting the compound (IX) or a salt thereof to conversion reaction of hydroxy to a leaving group.

This conversion reaction can be carried out by reacting the compound (IX) or a salt thereof with an agent such as thionyl halide (e.g. thionyl chloride, thionyl bromide, etc.), acyl halide such as sulfonyl halide (e.g. mesyl chloride, mesyl bromide, tosyl chloride, tosyl bromide, etc.), lower alkanoyl halide (e.g. acetyl chloride, acetyl bromide, etc.) or the like; or the like.

This reaction can be carried out in a solvent such as chloroform, methylene chloride, N,N-dimethylformamide, pyridine or any other solvent which does not adversely influence the reaction.

The reaction temperature is not critical and this reaction can be carried out under cooling to heating.

PROCESS D

The compound (XI) or a salt thereof can be prepared by reacting the compound (IV) or its reactive derivative at the carboxy group or a salt thereof with the compound (X) or its reactive derivative at the amino group or a salt thereof.

Suitable salts of the compounds (X) and (XI) can be referred to the ones as exemplified for the compound (I).

This reaction can be carried out in a similar manner to that of Process 2 mentioned in the above, and therefore the reaction mode and reaction conditions [e.g. base, catalyst, reactive derivative, solvent, reaction temperature, etc.] of this reaction are to be referred to those as explained in Process 2.

PROCESS E

The compound (XIb) or a salt thereof can be prepared by subjecting the compound (XIa) or a salt thereof to conversion reaction of halogen to hydroxy.

Suitable salts of the compounds (XIa) and (XIb) can be referred to the ones as exemplified for the compound (I).

This reaction can be carried out in a similar manner to that of Process 3 mentioned in the above, and therefore the reaction mode and reaction conditions of this reaction are to be referred to those as explained in Process 3.

PROCESS F

The compound (IX) or a salt thereof can be prepared by reacting the compound (XI) or a salt thereof with the compound (XII).

The reaction is usually carried out in a solvent such as methylene chloride, chloroform, diethyl ether, tetrahydrofuran, dimethyl sulfoxide or any other solvent which does not adversely influence the reaction.

The reaction is carried out preferably in the presence of an agent for the metalation of ω-lower alkynyl group such as cuprous halide (e.g. cuprous chloride, etc.) or the like.

The reaction temperature is not critical and the reaction is usually carried out at room temperature, under warming to heating.

The object compound (I) and a pharmaceutically acceptable salt thereof of this invention have anticholinergic activity and are useful for the treatment of dysuria or other diseases as mentioned before in human being and animals.

In the object compound (I) and a pharmaceutically acceptable salt thereof, side effect such as mydriasis or the like is alleviated.

In order to illustrate the usefulness of the object compound (I) and a pharmaceutically acceptable salt thereof, the pharmacological test data of the representative compounds of this invention are shown in the following.

TEST 1

Test on Inhibition of Urinary Bladder Contractions Induced by Water Filling in Rats

[I] Test Method

Male Sprague-Dawly rats, weighing 240–450 g, were anesthetized with urethane 1.0 g/kg s.c. The bladder was exposed through a midline incision in the abdomen for the recording of pressure within the bladder as follows; a balloon attached to one end of a stainless steel tube (O.D., 1.2 mm, 5 cm in length) was inserted into the bladder through a small incision in the bladder dome. The other end of the tube was connected to a pressure-transducer. The ureters were ligated and cut, and the proximal cut end was cannulated with polyethylene tubing and the urine was led outside.

Hyperactive urinary bladder (hyperactive contractions of the detrusor muscle) was induced by water filling of the bladder. Therefore, the balloon in the bladder was filled with water of a volume which caused a resting pressure of about 10 mmHg. Systemic blood pressure and heart rate were monitored from the common carotid artery.

When the contractile responses to water filling became constant, test compounds were administered intravenously.

[II] Test Compounds

Test Compound (1) : N-(4-Dimethylamino-2-butynyl)-2-cyclohexyl-2-hydroxy-2-phenylacetamide hydrochloride Test Compound (2) : N-(4-Dimethylamino-2-butynyl)-2-hydroxy-2,2-diphenylacetamide hydrochloride

[III] Test Results

The $ED_{30}$ value (mg/kg) of each Test Compound was as follows:

Test Compound (1) : $ED_{30} = 0.1$ (mg/kg)
Test Compound (2) : $ED_{30} = 0.068$ (mg/kg)

TEST 2

Anticholinergic effect on isolated guinea-pig strips

[1] Test Method

Male guinea-pigs, weighing 400–700 g, were stunned by a blow to the back of the head and were killed. Strips of bladder detrusor muscle (15–20 mm long×5 mm thick) were cut longitudinally and were suspended in an organ bath containing Krebs solution aerated with a gas mixture of 95% $O_2$:5% $CO_2$. Isometric contractions were recorded by means of an electromechanical displacement transducer. The strips were allowed to equilibrate for 10 min with five buffer change at 15 min intervals. Contraction was induced by 10 μM cabamylcholine. After the contraction became constant, the test drugs were added to the bath and the anticholinergic effects were evaluated. $IC_{50}$ values were calculated. $IC_{50}$ was defined as the concentration of drug that inhibited carbamylcholine response by 50%.

[II] Test Compound

Test compound (3): N(4-Ethylamino-2-butynyl)-2-hydroxy-2,2-diphenylacetamide hydrochloride

[III] Test Result

The $IC_{50}$ value (g/ml) was as follows.

$$IC_{50} = 5.8 \times 10^{-6} \text{ (g/ml)}$$

For therapeutic purpose, the compound (I) and a pharmaceutically acceptable salt thereof of this invention can be used in a form of pharmaceutical preparation containing said compound, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compound (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating pollakiuria. In general, amounts between 0.1 mg/body and about 1,000 mg/body may be administered per day.

The following Preparations and Examples are given for the purpose of illustrating this invention in more detail.

PREPARATION 1

A solution of 2-chloro-2-cyclohexyl-2-phenylacetyl chloride (9.0 g) in methylene chloride (50 ml) was added dropwise to a solution of 4-amino-2-butyn-1-ol hydrochloride (5.38 g) and triethylamine (30.8 ml) in methylene chloride (120 ml) at 0° C. The mixture was stirred at the same temperature for 10 minutes and then at room temperature for an additional 3.5 hours and 1N hydrochloric acid was added thereto. The organic layer was separated, washed with saturated sodium bicarbonate, aqueous solution, dried over magnesium sulfate, and evaporated in vacuo. The residue was purified by column chromatography on silica gel with a mixture of chloroform and ethyl acetate (6:1) as an eluent to give N-(4-hydroxy-2-butynyl)-2-chloro-2-cyclohexyl-2-phenylacetamide (7.32 g).

mp: 97 to 98° C.

IR (Nujol): 3400, 3250, 1650 cm$^{-1}$.

NMR (CDCl$_3$, δ): 1.00–1.90 (11H, m), 2.50–2.90 (1H, m), 3.93–4.13 (2H, m), 4.14–4.30 (2H, m), 6.83–7.16 (1H, broad m), 7.16–7.43 (3H, m), 7.53–7.73 (2H, m).

Mass: 3.19.

PREPARATION 2

A solution of N-(4-hydroxy-2-butynyl)-2-chloro-2-cyclohexyl-2-phenylacetamide (7.88 g) in a mixture of 1N-hydrochloric acid (85 ml) and 1,4-dioxane (180 ml) was heated at 90° C. for 45 minutes and evaporated in vacuo. To the residue was added water and extracted with ethyl acetate. The extract was washed successively with saturated sodium bicarbonate aqueous solution, water, and sodium chloride aqueous solution, dried over magnesium sulfate, and evaporated in vacuo. The residue was purified by column chromatography on silica gel with a mixture of chloroform and ethyl acetate (5:1) as an eluent to give N-(4-hydroxy-2-butynyl)-2-cyclohexyl-2-hydroxy-2-phenylacetamide as white powder (6.56 g).

mp: 121–122° C.

IR (Nujol) 3400, 1660 cm$^{-1}$.

NMR (CDCl$_3$, δ): 0.67–1.97 (10H, m), 2.00–2.23 (1H, m), 2.23–2.63 (1H, m), 2.83 (1H, s), 3.90–4.07 (2H, m), 4.07–4.30 (2H, m), 6.93 (1H, t, J=6Hz), 7.20–−0.50 (3H, m), 7.50–7.73 (2H, m).

Mass: 301, 188.

PREPARATION 3

Thionyl chloride (4.8 ml) was added dropwise to a mixture of N-(4-hydroxy-2-butynyl)-2-cyclohexyl-2-hydroxy-2-phenylacetamide (6.56 g) and N,N-dimethylformamide (5 drops) in dry chloroform (145 ml) at 0° C. and the reaction mixture was refluxed for 1 hour. The mixture was washed successively with water, 1N aqueous sodium hydroxide solution, and sodium chloride, aqueous solution, dried over magnesium sulfate, and evaporated in vacuo. The residue was purified by column chromatography on silica gel with a mixture of n-hexane and ethyl acetate (5:1) as an eluent to give N-(4-chloro-2-butynyl)-2-cyclohexyl-2-hydroxy-2-phenylacetamide as white powder (6.7 g).

mp: 65 to 71° C.

IR (Nujol) : 3400, 1660 cm$^{-1}$.

NMR (CDCl$_3$, δ): 0.67–2.17 (10H, m), 2.17–2.60 (1H, m), 2.60 (1H, s), 3.87–4.00 (2H, m), 4.00–4.13 (2H, m), 6.67–7.00 (1H, m), 7.10–7.50 (3H, m), 7.50–7.63 (2H, m).

PREPARATION 4

To a mixture of 4-amino-2-butyn-1-ol hydrochloride (4.33 g) and triethylamine (15 ml) in chloroform (50 ml) was added 2-chloro-2,2-diphenylacetyl chloride (9.12 g). After being stirred at room temperature for 2 hours, the mixture was washed with 1N hydrochloric acid and then water and evaporated in vacuo. To the oily residue were added 1N hydrochloric acid (25 ml) and 1,4-dioxane (50 ml) and the mixture was refluxed for 24 hours and then evaporated in vacuo. To the residue was added water and extracted with chloroform. The extract was washed with water, dried over magnesium sulfate, and evaporated in vacuo. The residue was purified by column chromatography on silica gel with a mixture of methylene chloride and ethyl acetate as an eluent to give N-(4-hydroxy-2-butynyl)-2-hydroxy-2,2-diphenylacetamide (4.12 g).

mp: 141 to 143° C .

IR (Nujol) : 3350, 3200, 1650 cm$^{-1}$.

NMR (DMSO-d$_6$, δ) : 3.95 (2H, dd, J=5.8Hz and 1.8Hz), 4.04 (2H, dd, J=5.9Hz and 1.8Hz), 5.14 (1H, t, J=5.9Hz), 6.76 (1H, s), 7.26–7.40 (10H, m), 8.44 (1H, t, J=5.8Hz).

Mass: 295, 278, 183.

PREPARATION 5

Thionyl chloride (0.81 ml) was added to a solution of N-(4-hydroxy-2-butynyl)-2-hydroxy-2,2-diphenylacetamide (3.32 g) and N,N-dimethylformamide (6 drops) in chloroform (20 ml) at room temperature. The mixture was stirred at 40° C. for 1 hour, washed with water, dried over magnesium sulfate, and evaporated in vacuo. The residue was purified by column chromatography on silica gel with a mixture of chloroform and ethyl acetate (5:1) as an eluent to give N-(4-chloro-2-butynyl)-2-hydroxy-2,2-diphenylacetamide (4.12 g) as oil.

IR (film) : 3380, 1650 cm$^{-1}$.

NMR (CDCl$_3$, δ): 3 67 (1H, s), 4.04–4.34 (4H, m), 6.65–6.98 (1H, broad m), 7.40 (10H, s).

Mass : 313, 296, 183.

EXAMPLE 1

A mixture of N-(4-chloro-2-butynyl)-2-cyclohexyl-2-hydroxy-2-phenylacetamide (0.5 g), sodium iodide (0.1 g), and 50% aqueous dimethylamine (1.5 ml) in 1,4-dioxane (5 ml) was stirred at room temperature overnight. After removal of the solvent, saturated sodium bicarbonate aqueous solution and ethyl acetate were added to the residue. The organic layer was separated, washed with sodium chloride aqueous solution, dried over magnesium sulfate, and evaporated in vacuo. The residue was purified by column chromatography on silica gel with a mixture of chloroform =nd methanol (20:1) as an eluent to give N-(4-dimethylamino-2-butynyl)-2-cyclohexyl -2-hydroxy-2-phenylacetamide (0.49 g) as oil.

IR (CHCl$_3$) : 3400, 1650 cm$^{-1}$.

NMR (CDCl$_3$, δ): 0.75–1.96 (11H, m), 2.09–2.49 (1H, m), 2.23 (6H, s), 3.13–3.25 (2H, m), 3.92–4.13 (2H, m), 6.64–6.98 (1H, broad m), 7.23–7.44 (3H, m), 7.50–7.69 (2H, m).

Mass : 329, 328, 189.

The following compounds (Examples 2 to 18) were obtained according to a substantially similar manner to that of Example 1.

EXAMPLE 2

N-(4-Methylamino-2-butynyl)-2-cyclohexyl-2-hydroxy-2-phenylacetamide

IR (CHCl$_3$) 3400, 1660 cm$^{-1}$. NMR (CDCl$_3$, δ): 0.67–2.23 (12H, m), 2.23–2.60 (1H, m), 2.67 (3H, s), 3.23–3.37 (2H, m), 3.83–4.10 (2H, m), 6.60–7.00 (1H, m), 7.10–7.50 (3H, m), 7.50–7.67 (2H, m).

Mass: 315, 313, 189.

EXAMPLE 3

N-(4-Ethylamino-2-butynyl)-2-cyclohexyl-2-hydroxy-2-phenylacetamide
IR (film): 3400, 1650 cm$^{-1}$.
NMR (CDCl$_3$, δ): 1.13 (3H, t, J=6Hz), 0.80-2.70 (13H, m), 2.67 (2H, q, J=6Hz), 3.34-3.47 (2H, m), 3.84-4.08 (2H, m), 6.57-6.97 (1H, broad m), 7.16-7.45 (3H, m), 7.45-7.78 (2H, m).
Mass : 328, 327, 189.

EXAMPLE 4

N-(4-Butylamino-2-butynyl)-2-cyclohexyl-2-hydroxy-2-phenylacetamide
IR (film): 3400, 1600 cm$^{-1}$.
NMR (CDCl$_3$, δ) : 0.70-2.00 (18H, m), 2.17-2.84 (3H, m), 3.30-3.46 (2H, m), 3.87-4.11 (2H, m), 6.60-6.94 (1H, broad m), 7.17-7.44 (3H, m), 7.44-7.70 (2H, m).
Mass : 357, 313, 189.

EXAMPLE 5

N-(4-t-Butylamino-2-butynyl)-2-cyclohexyl-2-hydroxy-2-phenylacetamide IR (CHCl$_3$): 3400, 1650 cm$^{-1}$.
NMR (CDCl$_3$, δ): 0.82-2.00 (10H, m), 1.10 (9H, s), 2.14-2.95 (2H, m) , 3.27-3.39 (2H, m), 3.86-4.04 (2H, m), 6.57-6.96 (1H, m), 7.16-7.43 (3H, m), 7.47-7.67 (2H, m).

EXAMPLE 6

N-(4-Cyclohexylamino-2-butynyl ]-2-cyclohexyl-2-hydroxy-2-phenylacetamide
IR [CHCl$_3$) : 3400, 1600 cm$^{-1}$.
NMR (CDCl$_3$, δ) : 0.63-2.10 (21H, m), 2.21-3.04 (3H, m), 3.35-3.46 (2H, m), 3.86-4.07 (2H, m), 6.63-6.99 (1H, broad m), 7.17-7.46 (3H, m), 7.46-7.73 (2H, m).
Mass: 383, 382, 189.

EXAMPLE 7

N-[4-(2-Hydroxyethyl)amino-2-butynyl]-2-cyclohexyl-2-hydroxy-2-phenylacetamide IR (CHCl$_3$) : 3400, 1650 cm$^{-1}$. NMR (CDCl$_3$, δ): 0.72-2.65 (14H, m), 2.72-2.88 (2H, m, 3.35-3.47 (2H, m), 3.56-3.74 (2H, m), 3.89-4.09 (2H, m), 6.75-7.06 (1H, broad m), 7.19-7.49 (3H, m), 7.49-7.72 (2H, m).
Mass: 345, 189.

EXAMPLE 8

N-[4-(Ethoxycarbonylmethyl)amino-2-butynyl]-2-cyclohexyl-2-hydroxy-2-phenylacetamide
IR (film): 3380, 1730, 1660 cm$^{-1}$.
NMR (CDCl$_3$, δ) : 0.71-1.93 (11H, m), 1.26 (3H, t, J=6Hz), 2.23-2.84 (2H, m), 3.33-3.51 (4H, m), 3.87-4.07 (2H, m), 4.16 (2H, q, J=6Hz), 6.60-6.98 (1H, broad m), 7.20-7.47 (3H, m), 7.49-7.75 (2H, m).
Mass 387, 386, 341, 313, 189.

EXAMPLE 9

N-[4-(N-Methyl)phenylamino-2-butynyl]-2-cyclohexyl-2-hydroxy-2-phenylacetamide
IR (CHCl$_3$) 3400, 1600 cm$^{-1}$. NMR (CDCl$_3$, δ): 0.70-1.97 (10H, m), 2.20-2.60 (1H, m), 2.67 (1H, s) 2.86 (3H, s), 3.80-4.10 (4H, m), 6.56-6.94 (3H, m), 7.06-7.46 (5H, m), 7.46-7.71 (2H, m).
Mass : 390, 189.

EXAMPLE 10

N-Ethyl)benzylamino-2-butynyl]-2-cyclohexyl-2-hydroxy-2-phenylacetamide
IR (film) : 3400, 1650 cm$^{-1}$.
NMR (CDCl$_3$, δ) : 0.73-2.00 (10H, m), 1.06 (3H, t, J=6Hz), 2.23-2.66 (1H, m), 2.50 (2H, q, J=6Hz), 2.74 (1H, s , 3.20-3.30 2H, m), 3.49 (2H, s), 3.88-4.12 (2H, m), 6.60-6.93 (1H, m), 7.06-7.46 (8H, m), 7.46-7.69 (2H, m).
Mass : 418, 417, 327, 189.

EXAMPLE 11

N-[4-{2-(3,4-Dimethoxyphenyl)ethylamino}-2-butynyl]-2-cyclohexyl-2-hydroxy-2-phenylacetamide
IR (film) 3420, 1660 cm$^{-1}$. NMR (CDCl$_3$, δ): 0.79-2.00 (12H, m), 2.13-2.44 (1H, m), 2.54-2.95 (4H, m), 3.26-3.42 (2H, m), 3.77 (6H, s), 3.77-4.03 (2H, m), 6.63-7.01 (4H, m), 7.19-7.50 (3H, m), 7.57-7.81 (2H, m).
Mass: 465, 313, 189.

EXAMPLE 12

N-[4-{N-Methyl-1-methyl-2-(4-methoxyphenyl)-ethylamino)-2-butynyl]-2-cyclohexyl-2-hydroxy-2-phenylacetamide
IR (film): 3400, 1660 cm$^{-1}$.
NMR (CDCl$_3$, δ): 0.90 (3H, d, J=6Hz), 0.70-1.83 (10H, m), 2.03-2.60 2H, m), 2.31 (3H, s , 2.67 (1H, s), 2.76-3.06 (2H, m), 3.26-3.40 (2H, m), 3.74 (3H, s), 3.86-4.10 (2H, m), 6.78 (2H, d, J=9Hz), 6.66-6.90 (1H, broad m) , 7.03 (2H, d, J=9Hz), 7.15-7.44 (3H, m), 7.50-7.66 (2H, m).
Mass : 462, 341, 189.

EXAMPLE 13

N-(4-Piperidino-2-butynyl)-2-cyclohexyl-2-hydroxy-2-phenylacetamide
IR (CHCl$_3$): 3400, 1660 cm$^{-1}$.
NMR (CDCl$_3$, δ): 0.67-2.20 (17H, m), 2.50 (4H, t, J=6Hz), 2.83 (1H, broad s), 3.27 (2H, m), 3.93-4.14 (2H, m), 6.70-7.01 (1H, m), 7.14-7 50 (3H, m), 7.50-7.76 (2H, m).
Mass: 368, 367, 189.

EXAMPLE 14

N-[4-(3 Azabicyclo[3.2.2]nonan-3-yl)-2-butynyl]-2-cyclohexyl-2-hydroxy-2-phenylacetamide
IR (CHCl$_3$) 3400, 1660 cm$^{-1}$.
NMR (CDCl$_3$, δ): 0.70-2.57 (21H, m), 2.57-2.76 (5H, m), 3.27-3.40 (2H, m), 3.87-4.14 (2H, m), 6.64-7.91 (1H, broad m), 7.23-7.47 (3H, m), 7.47-7.71 (2H, m).
Mass: 408, 407, 189, 124.

EXAMPLE 15

N-(4-Morpholino-2-butynyl)-2-cyclohexyl-2-hydroxy-2-phenylacetamide
IR (film) : 3400, 1660 cm$^{-1}$.
NMR (CDCl$_3$, δ): 0.70-2.00 (10H, m), 2.23-2.70 (5H, m), 2.87 (1H, broad s), 3.16-3.32 (2H, m), 3.60-3.86 4H, m), 3.90-4.13 (2H, m), 6.71-7.00 (1H, m), 7.10-7.44 (3H, m), 7.47-7.73 (2H, m)
Mass: 370, 369, 189.

EXAMPLE 16

N-[4-(4-Methyl-1-piperazinyl)-2-butynyl]-2-cyclohexyl-2-hydroxy-2-phenylacetamide
IR (film): 3400, 1660 cm$^{-1}$.

NMR (CDCl$_3$, δ): 0.74–2.24 (11H, m), 2.27 (3H, s), 2.24–2.72 (8H, m), 2.72–3.01 (1H, m), 3.17–3.30 (2H, m), 3.87–4.10 (2H, m), 6.70–7.00 (1H, broad m), 7.16–7.44 (3H, m), 7.46–7.76 (2H, m).

Mass: 383, 189.

EXAMPLE 17

N-[4-(4-Hydroxypiperidino)-2-butynyl]-2-cyclohexyl-2-hydroxy-2-phenylacetamide

NMR (CDCl$_3$, δ) : 0.60–2.93 (21H, m), 3.20 (2H, m), 3.50–3.86 (1H, m), 3.86–4.09 (2H, m), 6.70–7.03 (1H, m), 7.10–7.45 (3H, m), 7.45–7.73 (2H, m),

Mass : 384, 189.

EXAMPLE 18

N-[4-(2-Hydroxymethylpiperidino)-2-butynyl]-2-cyclohexyl-2-hydroxy-2-phenylacetamide IR (CHCl$_3$): 3400, 1660 cm$^{-1}$.

NMR (CDCl$_3$, δ): 0.73–2.06 (17H, m), 2.10–2.90 (5H, m), 3.09–3.88 (4H, m), 3.88–4.10 (2H, m), 6.73–6.96 (1H, m), 7.16–7.43 (3H, m), 7.50–7.70 (2H, m).

Mass : 398, 367, 189.

EXAMPLE 19

To a solution of N-(4-dimethylamino-2-butynyl)-2-cyclohexyl-2-hydroxy-2-phenylacetamide 0.48 g) in methanol (5 ml) was added 6.4N methanolic hydrogen chloride (1.5 ml) and the solution was evaporated in vacuo. The oily residue was crystallized from a mixture of isopropyl alcohol and ethyl acetate to give N-(4-dimethylamino-2-butynyl)-2-cyclohexyl-2-hydroxy-2phenylacetamide hydrochloride (0.3 g).

mp: 204 to 205° C .

IR (Nujol): 3420, 3300, 2400, 1640 cm$^{-1}$.

NMR (DMSO-d$_6$, δ): 0.86–1.86 (10H, m), 2.06–2.40 (1H, broad m), 2.60 (6H, s), 3.73–4.00 (4H, m), 5.51 (1H, s), 7.12–7.40 (3H, m), 7.43–7.64 (2H, m), 8.26 (1H, t, J=5Hz), 10.77–11.27 (1H, broad m).

Mass: 329, 328, 189.

The following compounds (Examples 20 to 36) were obtained according to a substantially similar manner to that of Example 19.

EXAMPLE 20

N-(4-Methylamino-2-butynyl)-2-cyclohexyl-2-hydroxy-2-phenylacetamide hydrochloride mp: 185–186° C . IR (Nujol): 3450, 3350, 2700, 2450, 1650 cm$^{-1}$.

NMR (CDCl$_3$, δ): 0.73–1.83 (10H, m), 2.00–2.40 (1H, m), 2.73 (3H, s), 3.67–3.93 (4H, m), 5.47 (1H, s), 7.10–7.37 (3H, m), 7.37–7.63 (2H, m), 8.13 (1H, t, J=6Hz), 9.13 (2H, broad s).

Mass: 315, 313, 189.

EXAMPLE 21

N-(4-Ethylamino-2-butynyl)-2-cyclohexyl-2-hydroxy-2-phenylacetamide hydrochloride mp: 197–198° C.

IR (Nujol): 3450, 3350, 2420, 1640 cm$^{-1}$.

NMR (DMSO-d$_6$, δ): 0.87–1.81 (10H, m), 1.15 (3H, t, J=6Hz), 2.07–2.43 (1H, broad m), 2.86 (2H, q, J=6Hz), 3.69–3.97 (4H, m), 5.51 (1H, s), 7.04–7.40 (3H, m), 7.40–7.67 (2H, m), 8.16 (1H, t, J=5Hz), 9.00–9.47 (2H, broad m).

Mass: 328, 327, 189.

EXAMPLE 22

N-(4-Butylamino-2-butynyl)-2-cyclohexyl-2-hydroxy-2-phenylacetamide hydrochloride IR (CHCl$_3$): 3370, 2750, 1650 cm$^{-1}$.

NMR (DMSO-d$_6$,δ): 0.76–1.89 (17H, m), 2.00–2.39 (1H, m), 2.85 (2H, t, J=7Hz), 3.76–4.06 (4H, m), 5.51 (1H, s), 7.13–7.42 (3H, m), 7.49–7.69 (2H, m), 8.16 (1H, t, J=5Hz), 8.86–9.26 (2H, broad m).

Mass: 357, 313, 189.

EXAMPLE 23

N-(4-t-Butylamino-2-butynyl)-2-cyclohexyl-2-hydroxy-2-phenylacetamide hydrochloride mp: 199–200° C.

IR (Nujol): 3350, 2660, 2500, 2460, 1660 cm$^{-1}$.

NMR (CD$_3$OD, δ): 0.84–1.93 (10H, m), 1.30 (9H, s), 2.20–2.61 (1H, m), 3.74–3.92 (2H, m), 3.92–4.07 (2H, m), 7.17–7.47 (3H, m), 7.47–7.71 (2H, m).

Mass: 357, 341, 189

EXAMPLE 24

N-(4-Cyclohex lamino-2-butynyl)-2-cyclohexyl-2-hydroxy-2-phenylacetamide hydrochloride mp: 171–172° C.

IR (Nujol): 3400, 2730, 2640, 2580, 2430, 1660 cm$^{-1}$.

NMR (DMSO-d$_6$, δ):0.83)-2.43 (21H, m), 2.80–3.20 (1H, m), 3.71–4.00 (4H, m), 3.51 (1H, s), 7.14–7.44 (3H, m), 7.44–7.68 (2H, m).

8.16 (1H, t, J=5Hz), 8.83–9.41 (2H, broad m).

Mass: 383, 382, 189.

EXAMPLE 25

N-[4-(2-Hydroxyethyl amino-2-butynyl]-2-cyclohexyl-2-hydroxy-2-phenylacetamide hydrochloride mp: 154–155° C.

IR (Nujol): 3350, 3200, 1660 cm$^{-1}$.

NMR (DMSO-d$_6$, δ): 0.80–1.89 (10H, m), 2.05–2.43 (1H, m), 2.95 (2H, t, J=5Hz), 3.62 (2H, broad q, J=5Hz), 3.75–4.03 (4H, m), 5.22 (1H, broad t, J=5Hz), 5.53 (1H, s), 7.15–7.42 (3H, m), 7.42–7.66 (2H, m), 8.17 (1H, broad t, J=5Hz), 8.96–9.32 (2H, broad m).

Mass: 345, 189.

EXAMPLE 26

N-[4-(Ethoxycarbonylmethyl)amino-2-butynyl]-2-cyclohexyl-2-hydroxy-2-phenylacetamide hydrochloride IR (CHCl$_3$) 3380, 2740, 1740, 1650 cm$^{-1}$.

NMR (DMSO-d$_6$, δ): 0.74–1.90 (10H, m), 1.24 (3H, t, J=6Hz), 2.06–2.39 (1H, broad m), 3.73–4.01 (6H, m), 4.20 (2H, q, J=6Hz), 5.35–5.63 (1H, broad m), 7.12–7.42 (3H, m), 7.42–7.64 (2H, m), 8.02–8.33 (1H, broad m), 9.39–9.99 (2H, broad m).

Mass : 387, 386, 341, 313, 189.

EXAMPLE 27

N-[4-(N-Methyl)phenylamino-2-butynyl]-2-cyclohexyl-2-hydroxy-2-phenylacetamide hydrochloride IR (CHCl$_3$) 3400, 2400, 1660 cm$^{-1}$.

NMR (CDCl$_3$, δ): 0.74–1.95 (10H, m), 2.30–2.70 (1H, m), 2.97 (3H, s), 3.90–4.10 (4H, m), 7.10–7.50 (2H, m), 7.23 (5H, s), 7.50–7.77 (4H, m)

Mass: 390, 189

EXAMPLE 28

N-[4-(N-Ethyl)benzylamino-2-butynyl]-2-cyclohexyl-2-hydroxy-2-phenylacetamide hydrochloride IR (Nujol): 3400, 3330, 2600, 1660 cm$^{-1}$.

NMR (DMSO-d$_6$, δ): 0.84–1.80 (13H, m), 2.10–2.60 (1H, m), 2.73–4.40 8H, m), 5.36–5.74 (1H, broad m), 7.13–7.67 (10H, m), 8.26–8.53 (1H, m), 10.90–11.34 (1H, broad m).

Mass: 418, 417, 327, 189.

EXAMPLE 29

N-[4-{2-(3,4-Dimethoxyphenyl)ethylamino}-2-butynyl]-2-cyclohexyl-2-hydroxy-2-phenylacetamide hydrochloride IR (CHCl$_3$) 3400, 2750, 2600, 1650 cm$^{-1}$.

NMR (DMSO-d$_6$, δ): 0.83–1.86 (10H, m), 2.14–2.40 (1H, m), 2.69–3.47 (4H, m), 3.73 (3H, s), 3.77 (3H, s), 3.70–3.99 (4H, m), 5.49 (1H, s), 6.63–7.03 (3H, m), 7.13–7.36 (3H, m), 7.45–7.57 (2H, m), 8.03–8.33 (1H, broad m), 9.02–9.34 (2H, broad m).

Mass: 465, 313, 189.

EXAMPLE 30

N-[4-{N-Methyl-1-methyl-2-(4-methoxyphenyl)-ethylamino}-2-butynyl]-2-cyclohexyl-2-hydroxy-2-phenylacetamide hydrochloride IR (CHCl$_3$): 3400, 2500, 1660 cm$^{-1}$.

NMR (DMSO-d$_6$, δ): 0.80–1.76 (13H, m), 2.13–3.40 (4H, m), 2.67 (3H, s), 3.73 (3H, s), 3.80–4.20 (4H, m), 5.50 (1H, s), 6.88 (2H, d, J=9Hz), 7.15 (2H, d, J=9Hz), 7.04–7.39 (3H, m), 7.46–7.64 (2H, m), 8.23 (1H, t, J=5Hz)

Mass 462, 341, 189

EXAMPLE 31

N-(4-Piperidino-2-butynyl)-2-cyclohexyl-2-hydroxy-2-phenylacetamide hydrochloride IR (CHCl$_3$) 3400, 2640, 2520, 1650 cm$^{-1}$.

NMR (DMSO-d$_6$, δ): 0.83–1.79 (16H, m), 2.10–2.40 (1H, broad m), 2.63–3.50 (4H, m), 3.75–4.03 (4H, m), 5.50 (1H, s), 7.12–7.40 (3H, m), 7.40–7.62 (2H, m), 8.23 (1H, t, J=5.0Hz), 10.36–10.97 (1H, broad m).

Mass: 368, 367, 189.

EXAMPLE 32

N-[4-{3-Azabicyclo[3.2.2]nonan-3-yl}-2-butynyl]-2-cyclohexyl-2-hydroxy-2-phenylacetamide hydrochloride IR (Nujol): 3420, 2600, 1660 cm$^{-1}$.

NMR (DMSO-d$_6$, δ): 0.78–3.67 (25H, m), 3.67–4.06 (4H, m), 5.37–5.67 (1H, broad m), 7.12–7.40 (3H, m), 7.40–7.64 (2H, m), 8.23 (1H, t, J=5Hz), 9.68–10.31 (1H, broad m).

Mass: 408, 407, 189, 124.

EXAMPLE 33

N-(4-Morpholino-2-butynyl)-2-cyclohexyl-2-hydroxy-2-phenylacetamide hydrochloride IR (CHCl$_3$) 3370, 2450, 1650 cm$^{-1}$.

NMR (DMSO-d$_6$, δ): 0.80–1.96 (10H, m), 2.10–2.34 (1H, broad m), 2.75–3.63 (4H, m), 3.64–4.08 (8H, m), 7.10–7.37 (3H, m), 7.41–7.67 (2H, m), 8.20 (1H, t, J=5.0Hz).

Mass: 370, 369, 189.

EXAMPLE 34

N-[4-(4-Methyl-1-piperazinyl)-2-butynyl]-2-cyclohexyl-2-hydroxy-2-phenylacetamide dihydrochloride IR (CHCl$_3$): 3400, 2400, 1640 cm$^{-1}$.

NMR (DMSO-d$_6$, δ): 0.77–1.89 (10H, m), 2.07–2.43 (1H, broad m), 2.78 (3H, s), 3.00–3.67 (8H, m), 3.77–3.98 (4H, broad m), 7.13–7.39 (3H, m), 7.46–7.70 (2H, m), 8.03–8.26 (1H, broad m).

Mass: 383, 189.

EXAMPLE 35

N-[4-(4-Hydroxypiperdino)-2-butynyl]-2-cyclohexyl-2-hydroxy-2-phenyloacetamide hydrochloride IR (CHCl$_3$): 3350, 2640, 2540, 1660 cm$^{-1}$, NMR (CDCl$_3$, δ): 0.60–2.77 (19H, m), 2.80–4.27 (7H, m), 7.03–7.70 (6H, m), 11.78–12.30 (1H, broad m).

Mass: 384, 189.

EXAMPLE 36

N-[4-(2-Hydroxymethylpiperidino)-2-butynyl]-2-cyclohexyl-2hydroxy-2-phenylacetamide hydrochloride IR (CHCl$_3$): 3350, 2650, 2450, 1660 cm$^{-1}$.

NMR (DMSO-d$_6$, δ): 0.84–2.02 (16H, m), 2.04–2.41 (1H, broad m), 2.70–4.09 (9H, m), 5.35–5.66 (2H, broad m), 7.13–7.43 (3H, m), 7.43–7.67 (2H, m), 8.28 (1H, t, J=5Hz), 9.78–10.26 (1H, broad m).

Mass: 398, 367, 289.

EXAMPLE 37

To a solution of 2-(cycanoimino)imidazolidine (0.28 g) in dimeythyl sulfoxide (10 ml) was added 60% sodium hydride dispersed in mineral oil (0.1 g) and the mixture was stirred at room temperature for 25 minutes. After an addition of N-(4-chloro-2-butynyl)-2-cyclohexyl-2-hydroxy-2-phenylacetamide (0.40 g), the mixture was stirred at the same temperature for further 45 minutes and then quenched with cold water (50 ml). The mixture was extracted with ethyl acetate (50 ml×3). The combined extracts were washed with sodium chloride aqueous solution, dried over magnesium sulfate, and evaporated in vacuo. The residue was purified by column chromatography on silica gel with a mixture of chloroform and methanol (20:1) as an eluent to give N-[4-{2-(cyanoimino)-1-imidazolidinyl}-2-butynyl]-2-cyclohexyl-2-hydroxy-2-phenylacetamide (0.37 g).

mp: 207 to 210° C.

IR (Nujol): 3300, 2170, 1650 cm$^{-1}$.

NMR (CD$_3$OD, δ): 0.92–1.90 (10H, m), 2.19–2.56 (1H, m), 3.21–3.40 (4H, m), 3.83–4.04 (4H, m), 7.12–7.43 (3H, m), 7.43–7.70 (2H, m).

Mass: 393, 310, 189.

EXAMPLE 38

A mixture of N-(4-chloro-2-butynyl)-2-hydroxy-2,2-diphenylacetamide (0.70 g), sodium iodide (0.1 g) and 50% aqueous dimethylamine (2.2 ml) in 1.4-dioxane (7 ml) was stirred at room temperature overnight and then evaporated in vacuo. After an addition of saturated sodium bicarbonate aqueous solution, the mixture was extracted with ethyl acetate. The extract was washed with water, dried over magnesium sulfate, and evaporated in vacuo. The residue was purified by column chromatography on silica gel with a mixture of chloroform and methanol (20:1) as an eluent to give N-(4- dimethylamino-2-butynyl)-2-hydroxy-2,2-diphenylacetamide (0.35 g).

mp: 103 to 104° C.

IR (CHCl$_3$): 3400, 1660 cm$^{-1}$.

NMR (CDCl$_3$, δ): 1.40–1.97 (1H, broad m), 2.22 (6H, s), 3.14–3.24 (2H, m), 4.06–4.22 (2H, m), 6.55–6.77 (1H, broad m), 7.23–7.56 (10H, m), Mass: 323, 322, 321, 183.

EXAMPLE 39

N-(4-Methylamino-2-butynyl)-2-hydroxy-2,2-diphenylacetamide was obtained according to a substantially similar manner to that of Example 38.

IR (CHCl$_3$): 3400, 3300, 1660 cm$^{-1}$.

NMR (CDCl$_3$, δ): 2.20–2.74 (2H, m), 2.32 (3H, s), 3.24–3.41 (2H, m), 3.98–4.20 (2H, m), 6.64–7.02 (1H, m), 7.23–7.61 (10H, m).

Mass: 307, 261, 183.

EXAMPLE 40

To a solution of N-(4-dimethylamino-2-butynyl)-2-hydroxy-2,2-diphenylacetamide (0.35 g) in methanol (5 ml) was added 6.4N methanolic hydrogen chloride (3ml) and the solution was evaporated in vacuo. The residue was dissolved in chloroform and the solution was evaporated in vacuo. The oily residue was crystalized from a mixture of isopropyl alcohol and ethyl acetate to give N-(4-dimethylamino-2-butynyl)-2-hydroxy-2,2-diphenylacetamide hydrochloride (0.21 g).

mp: 164 to 165° C.

IR (Nujol): 3300, 2700, 1650 cm$^{-1}$.

NMR (DMSO-d$_6$, δ): 2.65 (6H, s), 3.90–4.13 (4H, m), 6.59–6.94 (1H, m), 7.19–7.50 (10H, m), 8.53–8.76 (1H, m), 11.06 (1H, broad s).

Mass: 323, 322, 321, 183.

EXAMPLE 41

N-(4-Methylamino-2-butynyl)-2-hydroxy-2,2-diphenylacetamide hydrochloride was obtained according to a substantially similar manner to that of Example 40.

IR (CHCl$_3$): 3330, 2700, 2450, 1660 cm$^{-1}$.

NMR (DMSO-d$_6$, δ): 2.47 (3H, s), 3.80 (2H, s), 3.98 (2H, broad d, J=5Hz), 6.76 (1H, s), 7.05–7.50 (10H, m), 8.54 (1H, broad t, J=5Hz), 9.12–9.67 (1H, broad m).

Mass: 307, 261, 183.

EXAMPLE 42

A solution of N-(4-chloro-2-butynyl)-2-hydroxy-2,2-diphenylacetamide (1.0 g) and 70% aqueous ethylamine (4.32 g) in methanol (3 ml) was stirred at room temperature for 30 minutes and then evaporated in vacuo. The residue was dissolved in chloroform (30 ml) and the solution was washed with sodium chloride aqueous solution, dried over magnesium sulfate, and evaporated in vacuo. The residue was purified by column chromatography on silica gel with a mixture of chloroform and methanol (5:1) as an eluent to give N-(4-ethylamino-2-butynyl)-2-hydroxy-2,2-diphenylacetamide (0.8 g), which was treated with 4N methanolic hydrogen chloride to give N-(4-ethylamino-2-butynyl)-2-hydroxy-2,2-diphenylacetamide hydrochloride (0.65 g).

mp: 184 to 185° C.

IR (Nujol): 3400, 3300, 3220, 2650, 1650 cm$^{-1}$.

NMR (DMSO-d$_6$, δ): 1.16 (3H, t, J=7.0 Hz), 2.91 (2H, q, J=7.0 Hz), 3.83 (2H, s), 3.97 (2H, d, J=5.0 Hz), 7.16–7.47 (10H, m), 8.53 (1H, t, J=5 Hz), 8.87–9.60 (2H, broad m).

Mass: 323, 322, 183.

EXAMPLE 43

A solution of 4-diethylamino-2-butynylamine (0.14 g) in benzene (2.5 ml) was added dropwise to a solution of 2-chloro-2-cyclohexyl-2-phenylacetyl chloride (0.27 g) in benzene (2.5 ml below 25° C. After being stirred at room temperature for 19.5 hours, the resulting precipitates were collected by filtration and recrystallized from a mixture of acetone and diethyl ether to give N-(4-diethylamino-2-butynyl)-2-chloro-2-cyclohexyl-2-phenylacetamide hydrochloride (0.19 g).

mp: 148 to 152° C. (decomp.).

IR (Nujol): 3280, 2470, 2420, 1665 cm$^{-1}$.

NMR (CDCl$_3$, δ): 0.95–1.90 (16H, m), 2.50–3.25 (5H, m), 3.70–3.90 (2H, m), 3.90–4.10 (2H, m), 7.00–7.75 (6H, m), 12.65 (1H, broad s).

EXAMPLE 44

N-(4)-Diethylamino-2-butynyl)-2-chloro-2-cyclohexyl-2-phenylacetamide hydrochloride (100 mg) was dissolved in water (1 ml) and the solution was refluxed for 20 minutes. After being cooled, the solution Was made alkaline (pH 10) with saturated sodium bicarbonate aqueous solution and extracted with ethyl acetate. The extract was washed with sodium chloride aqueous solution, dried over sodium sulfate and evaporated in vacuo. The residue was purified by column chromatography on silica gel with a mixture of chloroform and methanol as an eluent to give N-(4-diethylamino-2-butynyl)-2-cyclohexyl-2-hydroxy-2-phenylacetamide (74 mg).

mp: 102 to 104° C.

IR (Nujol): 3400, 1665 cm$^{-1}$.

NMR (CDCl$_3$, δ): 1.03 (6H, t, J=7Hz), 0.60–1.90 (10H, m), 2.20–2.60 (1H, m), 2.48 (4H, q, J=7Hz), 3.03 (1H, s), 3.35 (2H, t, J=2Hz), 3.80–4.05 (2H, m), 6.86 (1H, t, J=5Hz), 7.13–7.70 (5H, m).

EXAMPLE 45

To a solution of N-(4-diethylamino-2-butynyl)-2-cyclohexyl-2-hydroxy-2-phenylacetamide (74 mg) in chloroform was added 4.1N methanolic hydrogen chloride (0.2 ml) and the mixture was evaporated in vacuo to give N-(4-diethylamino-2-butynyl)-2-cyclohexyl-2-hydroxy-2-phenylacetamide hydrochloride (90 mg) as oil.

IR (CHCl$_3$): 20, 2450, 1670 cm$^{-1}$.

NMR (CDCl$_3$, δ): 0.80–1.95 (16H, m), 2.30–3.25 (7H, m), 3.65–3.86 (2H, m), 3.86–4.10 (2H, m), 7.16–7.73 (5H, m), 9.40 (1H, broad s).

EXAMPLE 46

(1) A mixture of (S)-(+)-2-cyclohexyl-2-hydroxy-2-phenylacetic acid (1.13 g, 80% ee) and N,N'-carbonyldiimidazole (0.77 g) in chloroform (5 ml) was stirred at room temperature for 2 hours. After an addition of 4-dimethylamino-2-butynylamine (0.54 g), the mixture was stirred at the same temperature for an additional hour, then the mixture was poured into water, and extracted with ethyl acetate. The extract was washed with water and the organic layer was extracted with 1N-hydrochloric acid. The acidic solution was adjusted to pH 13 with aqueous solution of sodium hydroxide and extracted with ethyl acetate. The extract was washed with sodium chloride aqueous solution, dried over sodium sulfate and evaporated in vacuo. The residue was purified by column chromatography on silica gel with a mixture of chloroform and methanol (10:1) as an eluent to give (−)-N-(4-dimethylamino-2-butynyl)-2-cyclohexyl-2-hydroxy-2-phenylacetamide (0.60 g, 88% ee).

This compound was converted to an equimolar salt with L-tartaric acid as a crystal in a conventional manner.

(2) A small amount of the equimolar salt obtained above was added to a hot solution of racemic N-(4-dimethylamino -2-butynyl)-2-cyclohexyl-2-hydroxy-2-phenylacetamide (1.96 g) and L-tartaric acid (0.90 g) in a mixture of ethanol (5 ml) and methanol (1 ml). After the mixture was allowed to stand at room temperature for 2 hours, the resulting precipitates were collected by filtration and dried to give the equimolar salt of (−)-isomer (1.58 g). The mother liquor was evaporated in vacuo and the residue was made alkaline with aqueous solution of sodium hydroxide and extracted with ethyl acetate. The extract was washed with sodium chloride aqueous solution, dried over sodium sulfate and evaporated in vacuo to give (+)-N-(4-dimethylamino-2-butynyl)-2-cyclohexyl-2-hydroxy-2-phenylacetamide[0.91 g, $[\alpha]_D = +4.24°$ (C=7.8, EtOH), 81% ee], which was converted to 1/2(D-tartaric acid) salt of (+)-N-(4-dimethylamino-2-butynyl)-2-cyclohexyl-2-hydroxy-2-phenylacetamide in a conventional manner.

(3) 1/2(D-tartaric acid) salt of (+)-N-(4-dimethylamino-2-butynyl)-2-cyclohexyl-2-hydroxy-2-phenylacetamide obtained above (7.12 g) was added to a hot clear solution of racemic N-(4-dimethylamino-2-butynyl)-2-cyclohexyl-2-hydroxy-2-phenylacetamide (71.27 g) and D-tartaric acid (16.03 g) in a mixture of ethanol (350 ml) and methanol (50 ml). After the mixture was allowed to stand at room temperature for 6 hours, the resulting precipitates were collected by filtration, washed with ethanol (50 ml) and dried to give ½(D-tartaric acid) salt of (+)-N-(4-dimethylamino-2-butynyl)-2-cyclohexyl-2-hydroxy-2-phenylacetamide (39.07 g). The filtrate was evaporated in vacuo, and the residue was made alkaline with 10% sodium hydroxide aqueous solution and extracted with ethyl acetate. The extract was washed with sodium chloride aqueous solution, dried over sodium sulfate and evaporated in vacuo. To the residue were added ethanol (35 ml) and 20% ethanolic hydrogen chloride (35 ml) and then the alcoholic solution was treated successively with ethyl acetate (210 ml) and diisopropyl ether (70 ml). The resulting precipitates of hydrochloric acid salt of racemic N-(4-dimethylamino-2-butynyl)-2-cyclohexyl-2-hydroxy-2-phenylacetamide were removed by filtration and the filtrate was evaporated in vacuo. The residue was dissolved in ethyl acetate (50 ml) and stirred at room temperature for 4 hours. The resulting precipitates were collected by filtration and dried to give crude hydrochloric acid salt of (−)-N-(4-dimethylamino-2-butynyl)-2-cyclohexyl-2-hydroxy-2-phenylacetamide (11.24 g, 98% ee).

To the previously obtained 1/2(D-tartaric acid) salt of (+)-N-(4-dimethylamino-2-butynyl)-2-cyclohexyl-2-hydroxy-2-phenylacetamide (37.17 g) was added aqueous solution of sodium hydroxide and then extracted with ethyl acetate. The extract was washed with sodium chloride aqueous solution, dried over sodium sulfate and evaporated in vacuo to give (+)-N-(4-dimethylamino-2-butynyl)-2-cyclohexyl-2-hydroxy-2-phenylacetamide. This compound was similarly treated with ethanol (15 ml), 20% ethanolic hydrogen chloride (15 ml), ethyl acetate (75 ml) and diisopropyl ether (25 ml). After removal of the hydrochloric acid salt of racemic N-(4-dimethylamino-2-butynyl)-2-cyclohexyl-2-hydroxy-2-phenylacetamide, the filtrate was evaporated in vacuo and the residue was crystallized from ethyl acetate (50 ml) to give crude hydrochloric acid salt of (+)-N-(4-dimethylamino-2-butynyl)-2-cyclohexyl-2-hydroxy-2-phenylacetamide (10.05 g).

(4) Crude hydrochloric acid salt of (+)-N-(4-dimethylamino -2-butynyl)-2-cyclohexyl-2-hydroxy-2-phenylacetamide (5.74 g) was converted to the corresponding amine (5.58 g) by treatment of aqueous solution of sodium hydroxide. To the obtained amine (5.58 g) were added D-tartaric acid (1.08 g) and ethanol (100 ml) and the mixture was heated under reflux until a clear solution was obtained. After the mixture was allowed to stand at room temperature overnight, the resulting precipitates were collected by filtration, washed with ethanol (10 ml) and recrystallized twice from ethanol to give ½ (D-tartaric acid) salt of (+)-N-(4-dimethylamino-2-butynyl)-2-cyclohexyl-2-hydroxy-2-phenylacetamide (4.21 g).

mp: 188.0–188.5° C.

$[\alpha]_D^{≦} = -4.10°$ (C=1.75, MeOH).

IR (Nujol): 3460, 3360, 2725, 2660, 1660 cm$^{-1}$.

NMR (DMSO-d$_6$, δ): 0.89–1.42 (6H, m), 1.42–1.81 (4H, m), 2.18 (6H, s), 2.21–2.39 (1H, m), 3.26 (2H, s), 3.70–4.00 (2H, m), 4.21 (1H, s), 5.31–5.80 (1H, broad s), 7.16–7.40 (3H, m), 7.53–7.63 (2H, m), 8.16 (1H, t, J=5.8Hz).

Mass: 329, 328, 189.

½(L-Tartaric acid) salt of (−)-N-(4-dimethylamino-2-butynyl)-2-cyclohexyl-2-hydroxy-2-phenylacetamide was obtained according to a similar manner to that used for obtaining ½(D-tartaric acid) salt of (+) isomer.

mp: 188.0–188.5° C.

$[\alpha]_D^> = +3.69°$ (C=1.67, MeOH).

IR (Nujol): 3460, 3360, 2725, 1660 cm$^{-1}$.

NMR (DMSO-d$_6$, δ): 0.87–1.42 (6H, m), 1.46–1.77 (4H, m), 2.15 (6H, s), 2.17–2.34 (1H, m), 3.22 (2H, s), 3.67–3.95 (2H, m), 4.18 (1H, s), 5.20–5.69 (1H, broad s), 7.13–7.36 (3H, m), 7.49–7.63 (2H, m), 8.12 (1H, t, J=5.8Hz).

Mass: 329, 328, 189.

(5) ½(D-Tartaric acid) salt of (+)-N-(4-dimethylamino-2-butynyl)-2-cyclohexyl-2-hydroxy-2-phenylacetamide (1.34 g) was added to 10% sodium hydroxide aqueous solution (1.6 ml) and extracted with ethyl acetate. The extract was washed with sodium chloride aqueous solution, dried over sodium sulfate and evaporated in vacuo to give (+)-N-(4-dimethylamino-2-butynyl) -2-cyclohexyl-2-hydroxy-2-phenylacetamide (1.09 g).

mp: 120.5–121.0° C.

$[\alpha]_D^{22} = +5.21$ (C=5.28, EtOH)

IR (Nujol): 3400, 3320, 1660 cm$^{-1}$.

NMR (CDCl$_3$, δ): 0.73–1.50 (6H, m), 1.59–1.89 (4H, m), 2.23 (6H, s), 2.44 (1H, t, J=11.7Hz), 2.86 (1H, s), 3.19 (2H, t, J=1.9Hz), 3.92 (1H, dd, J=17.4Hz and 5.1Hz), 4.08 (1H, dd, J=17.4Hz and 5.1Hz), 6.87 (1H, t, J=5.1Hz), 7.20–7.41(3H, m), 7.56–7.65 (2H, m).

Mass: 329, 328, 189.

(−)-N-(4-Dimethylamino-2-butynyl)-2-cyclohexyl-2-hydroxy-2-phenylacetamide was obtained according to a similar manner to that used for obtaining the corresponding (+) isomer.

mp: 121.0–122.5° C.

$[\alpha]> = -4.85°$ (C=5.11, EtOH).

IR (Nujol): 3400, 3320, 1660 cm$^{-1}$.

NMR (CDCl$_3$, δ): 0.74–1.52 (6H, m), 1.58–1.93 (4H, m), 2.23 (6H, s), 2.43 (1H, t, J=11.8Hz), 2.94 (1H, s), 3.18 (2H, t, J=1.9Hz), 3.92 (1H, dd, J=17.4Hz and 5.1Hz), 4.08 (1H, dd, J=17.4Hz and 5.1Hz), 6.88 (1H, t, J=5.1Hz), 7.21–7.41 (3H, m), 7.56–7.67 (2H, m).

Mass: 329, 328, 189.

(6) To a solution of (+)-N-(4-dimethylamino-2-butynyl)-2-cyclohexyl-2-hydroxy-2-phenylacetamide (1.01 g) in ethanol (15 ml) was added 20% ethanolic hydrogen chloride (1 ml) and the solution was evaporated in vacuo. The residue was dissolved in ethyl acetate and the solution was stirred at room temperature overnight. The resulting precipitates were collected by filtration, washed with ethyl acetate and dried in a desiccator to give hydrochloric acid salt of (+)-N-(4-dimethylamino-2-butynyl)-2-cyclohexyl-2-hydroxy-2-phenylacetamide (0.99 g).

mp: 170.5–171.0° C.

[α]$_D^{23}$ = +3.92° (C=3.67, MeOH).

IR (Nujol): 3330, 2560, 2400, 1660, 1650 cm$^{-1}$.

NMR (DMSO-d$_6$, δ): 0.88–1.83 (10H, m), 2.15–2.39 (1H, m), 2.63 (6H, s), 3.88, (2H, d, J=5.6Hz), 3.96 (2H, s), 5.60 (1H, s), 7.13–7.38 (3H, m), 7.52–7.65 (2H, m), 8.35 (1H, t, J=5.6Hz), 11.18 (1H, s).

Mass: 329, 328, 189.

Hydrochloric acid salt of (−)-N-(4-dimethylamino-2-butynyl)-2-cyclohexyl-2-hydroxy-2-phenylacetamide was obtained according to a similar manner to that used for obtaining the corresponding (+) isomer.

mp: 171.5–173.0° C.

[α]$_D^{23}$ = −3.93° (C=3.83, MeOH).

IR (Nujol): 3340, 2380, 1660, 1650 cm$^{-1}$.

NMR (DMSO-d$_6$, δ): 0.88–1.79 (6H, m), 2.16–2.40 (1H, m), 2.63 (6H, s), 3.88 (2H, d, J=5.6Hz), 3.96 (2H, s), 5.59 (1H, s), 7.15–7.38 (3H, m), 7.50–7.64 (2H, m), 8.35 (1H, t, J=5.6Hz), 11.06 (1H, s).

Mass: 329, 328, 189.

PREPARATION 6

A solution of 4-acetylaminomethylpyridine (22.40 g) and ethyl iodide (17.9 ml) in acetone (300 ml) was heated under reflux for 24 hours and then the solvent was evaporated in vacuo. The residue was washed with a mixture of n-hexane, ethyl acetate and ethanol to give very hygroscopic 4-acetylaminomethyl-1-ethylpyridinium iodide (42.18 g), which was used without further purification.

PREPARATION 7

Sodium borohydride (21.96 g) was added portionwise to a solution of 4-acetylaminomethyl-1-ethylpyridinium iodide (44.43 g) in methanol (400 ml) below 20° C. and the mixture was stirred at 75° C. for 3 hours. The mixture was evaporated in vacuo and the residue was poured into 0.7N aqueous solution of sodium hydroxide (115 ml). The mixture was extracted with methylene chloride. The extracts were washed with brine, dried over magnesium sulfate and evaporated in vacuo. The residue was purified by vacuum distillation to give 4-acetylaminomethyl-1-ethyl-1,2,3,6-tetrahydropyridine (23.38 g).

bp: 143–145° C./0.3mmHg.

IR (film): 3300, 3080, 1650 cm$^{-1}$.

NMR (CDCl$_3$, δ): 1.11 (3H, t, J=6Hz), 1.97 (3H, s), 1.86–2.33 (2H, m), 2.33–2.76 (4H, m), 2.96 (2H, broad s), 3.70–3.90 (2H, m), 5.53 (1H, m), 5.70–6.20 (1H, broad s).

Mass: 182, 167.

PREPARATION 8

A solution of 4-acetylaminomethyl-1-ethyl-1,2,3,6-tetrahydropyridine (20.0 g) and 6N aqueous solution of sodium hydroxide (73 ml) in methanol (150 ml) was refluxed for 40 hours. The solution was acidified with concentrated hydrochloric acid under ice cooling and evaporated in vacuo. To the residue was added ethanol (400 ml) and the mixture was refluxed for an hour. The resulting precipitates were filtered off and the filtrate was evaporated in vacuo. The residue was treated with Amberlite IRA-910 (trademark: Rohm & Haas Co.) and purified by vacuum distillation to give 4-aminomethyl-1-ethyl-1,2,3,6-tetrahydropyridine (14.25 g).

bp: 87° C./14mmHg.

IR (film): 3360, 3270, 1600 cm$^{-1}$.

NMR (CDCl$_3$, δ): 1.10 (3H, t, J=6Hz), 0.97–1.40 (2H, m), 2.00–2.30 (2H, m), 2.30–2.70 (4H, m), 2.83–3.06 (2H, m), 3.17 (2H, s), 5.46–5.67 (1H, m).

Mass: 140, 123, 110.

PREPARATION 9

To a solution of 2-chloro-2,2-diphenylacetyl chloride (321.21 g) in chloroform (321 ml) was added a mixture of 2-propynylamine (64.11 g) and triethylamine (125.14 g) in chloroform (125 ml) below 25° C. After being stirred at room temperature for 30 minutes, the reaction mixture was washed with water and evaporated in vacuo. To the residue were added 0.3N-hydrochloric acid (320 ml) and 1,4-dioxane (320 ml), then the mixture was refluxed for an hour. The mixture was extracted with ethyl acetate and the extracts were evaporated in vacuo. The residue was dissolved in chloroform. The solution was washed successively with 3% aqueous solution of sodium hydroxide and brine, dried over magnesium sulfate, and evaporated in vacuo. The residue was washed with diisopropyl ether and dried to give N-(2-propynyl)-2-hydroxy-2,2-diphenylacetamide (252.05 g).

mp: 105 to 106° C.

IR (Nujol): 3400, 3280, 2110, 1660 cm$^{-1}$.

NMR (CDCl$_3$3, δ): 2.24 (1H, t, J=2.6Hz), 3.72 (1H, s), 4.05 (2H, dd, J=5.4Hz and 2.6Hz), 6.78 (1H, broad m), 7.22–7.51 (10H, m).

Mass: 265, 183.

PREPARATION 10

A mixture of N-(2-propynyl)-2-hydroxy-2,2-diphenylacetamide (165.2 g), cuprous chloride (2.50 g) and potassium carbonate (1.73 g) in dimethylsulfoxide (330 ml) was stirred at 75° C. for 45 minutes under a nitrogen atmosphere. To the reaction mixture was added paraformaldehyde (25.3 g) and the mixture was stirred at 85° C. for 5 hours. The reaction mixture was poured into the mixture of 5% hydrochloric acid and 10% aqueous solution of sodium chloride (1:5), and extracted with ethyl acetate. The extracts were washed successively with brine, 5% aqueous solution of sodium thiosulfate and brine, dried over magnesium sulfate and evaporated in vacuo. To the residue was added a mixture of diisopropyl ether and chloroform (1:1) (100 ml) and the mixture was stirred at room temperature for 30 minutes. The resulting precipitates were collected by filtration, washed with a mixture of diisopropyl ether and chloroform (1:1) and dried to give N-(4-hydroxy-2-butynyl)-2-hydroxy-2,2-diphenylacetamide (119.7 g).

mp: 141 to 143° C.

IR (Nujol): 3350, 3200, 1650 cm$^{-1}$.

PREPARATION 11

A solution of methyl benzoylformate (0.50 g) and 4-dimethylamino-2-butynylamine (0.38 g) in methanol (5 ml) was refluxed for 3 hours. To the reaction mixture was added 1N aqueous solution of sodium hydroxide and the mixture was extracted with ethyl acetate. The extract was washed with brine, dried over magnesium sulfate and evaporated in vacuo. The residue was purified by column chromatography on silica gel with a mixture of chloroform and methanol (20:1) as an eluent to give N-(4-dimethylamino-2-butynyl)benzoylformamide (0.39 g).

mp: 51-53° C.

IR (film): 3300, 1670 cm$^{-1}$.

NMR (CDCl$_3$, δ): 2.30 (6H, s), 3.25 (2H, t, J=2.0Hz), 4.22 (2H, dt, J=5.5Hz and 2.0Hz), 7.19-7.35 (1H, broad), 7.49 (2H, t, J=7.4Hz), 7.64 (1H, t, J=7.4Hz), 8.35 (2H, d, J=7.4Hz).

Mass: 244, 105.

The following compounds (Examples 47 to 51) were obtained according to a similar manner to that of Example 1.

EXAMPLE 47

N-[4-(N-Methylethylamino)-2-butynyl]-2-cyclohexyl-2-hydroxy-2-phenylacetamide

IR (film): 3400, 3070, 1660 cm$^{-1}$. NMR (CDCl$_3$, δ): 0.69-1.50 (6H, m), 1.04 (3H, t, J=7.2Hz), 1.58-1.89 (4H, m), 2.24 (3H, s), 2.41 (2H, q, J=7.2Hz), 2.32-2.53 (1H, broad m), 2.81 (1H, s), 3.27 (2H, t, J=2.0Hz), 3.91 (1H, dd, J=17.4Hz and 5.1Hz), 4.07 (1H, dd, J=17.4Hz and 3.4 Hz), 6.77-6.95 (1H, m), 7.22-7.45 (3H, m), 7.56-7.69 (2H, m).

Mass : 342 (M+), 327, 285, 189.

EXAMPLE 48

N-(4-Propylamino-2-butynyl)-2-hydroxy-2,2-diphenylacetamide mp: 135-136° C.

Nujol): 3370, 3280, 1660 cm$^{-1}$.

NMR (CDCl$_3$, δ): 0.91 (3H, t, J=7.3Hz), 1.47 (2H, qt, J=7.3Hz and 7.1Hz), 1.07-2.18 (1H, broad m), 2.56 (2H, t, J=7.1Hz), 3.36 (2H, t, J=2.0Hz), 4.11 (2H, dt, J=5.3Hz and 2.0Hz), 6.76 (1H, J=5 3Hz, broad t), 7.19-7.53 (10H, m).

Mass: 336, 335 (M-1), 289, 261, 183.

EXAMPLE 49

N-(4-Cyclopropylamino-2-butynyl)-2-hydroxy-2,2-diphenylacetamide

IR (CHCl$_3$): 3400, 3050, 3000, 1660, 1600 cm$^{-1}$.

NMR (CDCl$_3$, δ): 0.29-0.55 (4H, m), 1.45-2.15 (1H, broad s), 2.19-2.37 (1H, m), 3.41 (2H, t, J=2.0Hz), 4.11 (2H, dt, J=5.3Hz and 2.0Hz), 6.68 (1H, J=5.3Hz, broad t), 7.21-7.55 (10H, m).

Mass: 334, 333 (M-1), 261, 217, 183.

EXAMPLE 50

N-[4-(N-Methylethylamino)-2-butynyl]-2-hydroxy-2,2-diphenylacetamide

IR (CHCl$_3$) 3400, 1660, 1600 cm$^{-1}$.

NMR (CDCl$_3$, δ): 1.04 (3H, t, J=7.2Hz), 2.23 (3H, s), 2.40 (2H, q, J=7.2Hz), 3.26 (2H, t, J=2.0Hz), 4.12 (2H, dt, J=5.3Hz and 2.0Hz), 3.90-4.10 (1H, broad m), 6.69 (1H, broad s), 7.26-7.46 (10H, m).

Mass: 336, 321, 183.

EXAMPLE 51

N-[4-(N-Methyl-2-hydroxyethylamino)-2-butynyl]-2-hydroxy-2,2-diphenylacetamide mp: 152-153° C.

IR (Nujol): 3350, 3170, 1630 cm$^{-1}$.

NMR (DMSO-d$_6$, δ): 2.17 (3H, s), 2.40 (2H, t, J=6.2Hz), 3.27 (2H, s), 3.44 (2H, td, J=6.2Hz and 5.5Hz), 3.93 (2H, d, J=5.8Hz), 4.39 (1H, t, J=5.5Hz), 6.73 (1H, s), 7.20-7.47 (10H, m), 8.46 (1H, t, J=5.8Hz).

Mass: 352 (M+), 321, 260, 183.

The following compounds (Examples 52 to 56) were obtained according to a similar manner to that of Example 43.

EXAMPLE 52

N-[2-(Diethylamino)ethyl]-2-chloro-2-cyclohexyl-2-phenylacetamide

IR (film): 3380, 1660 cm$^{-1}$.

NMR (CDCl$_3$, δ): 0.80-1.90 (10H, m), 0.97 (6H, t, J=6.0Hz), 2.30-2.60 (6H, m), 2.60-2.90 (1H, m), 3.00-3.47 (2H, m), 7.23-7.40 (3H, m), 7.40-7.63 (1H, m), 7.63-7.83 (2H, m).

Mass: 350 (M+), 314.

EXAMPLE 53

N-(1-Ethyl-1,2,3,6-tetrahydropyridin-4-yl)methyl-2-chloro-2-cyclohexyl-2-phenylacetamide IR (film): 3440, 3370, 1670, 1600 cm$^{-1}$.

NMR (CDCl$_3$, δ): 0.94-1.55 (6H, m), 1.11 (3H, t, J=7.2Hz), 1.55-1.88 (4H, m), 1.88-2.19 (2H, m), 2.41-2.64 (2H, m), 2.47 (2H, q, J=7.2Hz), 2.72 (1H, m), 2.94 (2H, s), 3.70 (1H, dd, J=15.2Hz and 5.0Hz), 3.85 (1H, dd, J=15.2Hz and 5.0Hz), 5.44 (1H, s), 6.90 (1H, m), 7.23-7.45 (3H, m), 7.62-7.82 (2H, m).

Mass: 376, 374, 338.

EXAMPLE 54

N-(4-Dimethylamino-2-butynyl)-2-chloro-2,2-bis(2-chlorophenyl)acetamide

IR (CHCl$_3$): 3430, 3350, 1670 cm$^{-1}$.

NMR (CDCl$_3$, δ): 2.29 (6H, s), 3.26 (2H, t, J=2.0Hz), 4.26 (2H, dt, J=5.3Hz and 2.0Hz), 7.17-7.55 (9H, m).

Mass: 412, 410, 408.

EXAMPLE 55

N-(4-Dimethylamino-2-butynyl)-2-hydroxy-2,2-bis(4-methoxyphenyl)acetamide

IR (CHCl$_3$) 3410, 2050, 1670, 1610 cm$^-$.

NMR (CDCl$_3$, δ): 2.22 (6H, s), 3.18 (2H, s), 3.80 (6H, s), 4.09-4.14 (2H, m), 6.71-6.81 (1H, broad m), 6.85 (4H, d, J=8.9Hz), 7.35 (4H, d, J=8.9Hz).

Mass: 382 (M+), 364, 339, 243.

EXAMPLE 56

N-(4-Dimethylamino-2-butynyl)-9-xanthenecarboxamide

IR (Nujol): 3300, 1640 cm$^{-1}$.

NMR (DMSO-d$_6$, δ) : 2.13 (6H, s), 3.17 (2H, s), 3.89 (2H, d, J=5.3Hz), 4.94 (1H, s), 7.03-7.20 (4H, m), 7.23-7.40 (4H, m), 8.86 (1H, t, J=5.3Hz).

Mass: 320 (M+), 277, 208, 181.

EXAMPLE 57

A mixture of N-[2-(diethylamino)ethyl]-2-chloro-2-cyclohexyl-2-phenylacetamide (6.35 g) and 1N hydrochloric acid (100 ml) was heated at 55° C. for 2 hours. After being cooled, the solution was made alkaline with 6N aqueous solution of sodium hydroxide and extracted with ethyl acetate. The extract was dried over magnesium sulfate, evaporated under reduced pressure. And the residue was triturated with a mixture of n-hexane and diisopropyl ether to give N-[2-(diethylamino)ethyl]-2-cyclohexyl-2-hydroxy-2-phenylacetamide (4.98 g).

mp: 145–150° C.
IR (Nujol): 3360, 1660 cm$^{-1}$.
NMR (CDCl$_3$, δ): 0.73–1.90 (10H, m), 1.00 (6H, t, J=6.0Hz), 2.10–2.66 (7H, m), 3.30 (2H, q, J=6.0Hz), 3.50 (1H, s), 6.83–7.23 (1H, broad s), 7.23–7.50 (3H, m), 7.57–7.73 (2H, m).

The following compounds (Examples 58 and 59) were obtained according to a similar manner to that of Example 57.

EXAMPLE 58

N-(1-Ethyl-1,2,3,6-tetrahydropyridin-4-yl)methyl-2-cyclohexyl-2-hydroxy-2-phenylacetamide IR (film): 3400, 1660, 1600 cm$^{-1}$.
NMR (CDCl$_3$, δ): 0.60–2.60 (13H, m), 1.10 (3H, t, J=7Hz), 2.43 (2H, q, J=7Hz), 2.48 (2H, t, J=6Hz), 2.70–3.04 (3H, broad m), 3.61–3.84 (2H, broad m), 5.27–5.47 (1H, m), 6.64 (1H, t, J=5Hz), 7.17–7.47 (3H, m), 7.47–7.71 (2H, m).
Mass: 356, 189.

EXAMPLE 59

N-(4-Dimethylamino-2-butynyl)-2-hydroxy-2,2-bis(2-chlorophenyl)acetamide

IR (CHCl$_3$): 3550, 3400, 1680 cm$^{-1}$.
NMR (CDCl$_3$, δ): 2.27 (6H, s), 3.23 (2H, t, J=1.9Hz), 4.22 (2H, dt, J=5.4Hz and 1.9Hz), 4.86 (1H, broad s), 7.14 (1H, t, J=5.4Hz), 7.18–7.48 (8H, m).
Mass: 393, 392, 391, 390, 347, 329, 251, 199.

EXAMPLE 60

A mixture of 2-cyclopentyl-2-hydroxy-2-phenylacetic acid (2.50 g), phosphorus pentachloride (5.20 g) and toluene (10 ml) was heated at 90° C. for 2 hours. After being cooled, the solution was evaporated under reduced pressure and coevaporated several times with toluene. The residue was dissolved in chloroform (10 ml) and the solution was added dropwise to a solution of 4-dimethylamino-2-butynylamine (1.21 g) and triethylamine (1.6 ml) in chloroform (10 ml) at 0–5 ° C. After being stirred for 17.5 hours at room temperature, the solution was made alkaline with 1N aqueous solution of sodium hydroxide and extracted with chloroform. The extract was washed with brine, dried over magnesium sulfate, and evaporated in vacuo. To the residue, 1N hydrochloric acid (20 ml) and 1,4-dioxane (40 ml) were added and heated at 90° C. for 40 minutes. After being cooled, the solution was made alkaline with 1N aqueous solution of sodium hydroxide and extracted with ethyl acetate. The extract was washed with brine, dried over magnesium sulfate and condensed under reduced pressure. The residue was purified by column chromatography on silica gel with a mixture of chloroform and methanol as an eluent to give N-(4-dimethylamino-2-butynyl)-2-cyclopentyl-2-hydroxy-2-phenylacetamide (0.98 g).

IR (film): 3400, 1650, 1600 cm$^{-1}$.
NMR (CDCl$_3$, δ): 1.04–1.32 (1H, m), 1.39–1.79 (7H, m), 2.23 (6H, s), 2.95–3.25 (2H, m), 3.17 (2H, t, J=1.9Hz), 3.86–4.14 (2H, m), 6.69 (1H, m), 7.20–7.30 (3H, m), 7.54–7.69 (2H, m).
Mass: 314, 175.

The following compounds (Examples 61 to 67) were obtained according to a similar manner to that of Example 60.

EXAMPLE 61

N-(4-Dimethylamino-2-butynyl)-2-cycloheptyl-2-hydroxy-2-phenylacetamide mp: 114–115° C.
IR (Nujol): 3310, 1660 cm$^{-1}$.
NMR (CDCl$_3$, δ): 0.95–1.80 (12H, m), 2.23 (6H, s), 2.50–2.79 (2H, m), 3.13–3.26 (2H, m), 3.92 (1H, dd, J=17.4Hz and 5.1Hz), 4.08 (1H, dd, J=17.4Hz and 5.5Hz), 6.76–6.96 (1H, m), 7.42–7.46 (3H, m), 7.55–7.72 (2H, m).
Mass: 342 (M ), 203.

EXAMPLE 62

N-(1-Methyl-1,2,3,6-tetrahydropyridin-4-yl)methyl-2-cyclohexyl-2-hydroxy-2-phenylacetamide mp: 127–129° C.
IR (Nujol): 3300, 3050, 1660, 1600 cm$^{-1}$.
NMR (CDCl$_3$, δ): 0.75–2.15 (12H, m), 2.32 (3H, s), 2.47 (2H, t, J=5.8Hz), 2.24–2.52 (1H, m), 2.79–3.00 (3H, broad m), 3.67 (1H, dd, J=15.6Hz and 5.7Hz), 3.80 (1H, dd, J=15.6Hz and 5.7Hz), 5.38 (1H, broad s), 6.64 (1H, J=5.7Hz, broad t), 7.20–7.45 (3H, m), 7.54–7.70 (2H, m).
Mass: 342 (M+), 189.

EXAMPLE 63

N-(1-Ethylpiperidin-4-yl)methyl-2-cyclohexyl-2-hydroxy-2-phenylacetamide mp: 114–115° C.
IR (Nujol): 3400, 3300, 1650 cm$^{-1}$.
NMR (CDCl$_3$, δ): 0.77–2.05 (17H, m), 1.09 (3H, t, J=7.2Hz), 2.42 (2H, q, J=7.2Hz), 2.19–2.69 (1H, m), 2.86–3.30 (5H, m), 6.74 (1H, J=5.6Hz, broad t), 7.17–7.44 (3H, m), 7.54–7.68 (2H, m).
Mass: 358, 343, 275, 189.

EXAMPLE 64

N-(1-Benzyl-1,2,3,6-tetrahydropyridin-4-yl)methyl-2-cyclohexyl-2-hydroxy-2-phenylaetamide mp: 141–142° C.
IR (Nujol): 3410, 3270, 1660, 1600 cm$^{-1}$.
NMR (CDCl$_3$, δ): 0.78–1.88 (10H, m), 1.97 (2H, broad s), 2.31–2.61 (1H, m), 2.51 (2H, t, J=5.8Hz), 2.86 (1H, s), 2.92 (2H, broad s), 3.55 (2H, s), 3.66 (1H, dd, J=15.2Hz and 5.2Hz), 3.82 (1H, dd, J=15.2Hz and 5.2Hz), 5.36 (1H, broad s), 6.64 (1H, t, J=5.8Hz), 7.19–7.44 (8H, m), 7.53–7.67 (2H, m).
Mass: 418 (M+), 327, 282, 189, 172, 91.

EXAMPLE 65

N-(4-Dimethylamino-2-butynyl)-2-hydroxy-2,2-bis(4-methylphenyl)acetamide mp: 138–139° C .
IR (CHCl$_3$): 3400, 1660, 1610 cm$^{-1}$.
NMR (CDCl$_3$, δ): 1.52–1.92 1H, broad s , 2.21 (6H, s), 2.34 (6H, s), 3.17 (2H, t, J=2.0Hz), 4.11 (2H, dt, J=5.4Hz and 2.0Hz), 6.73 (1H, t, J=5.4Hz), 7.06–7.19 (4H, m), 7.24–7.39 4H, m).
Mass: 350 (M+), 332, 289, 211.

EXAMPLE 66

N-(1-Ethyl-1,2,3,6-tetrahydropyridin-4-yl)methyl-2-hydroxy-2,2-diphenylacetamide mp: 102-108° C.

IR (Nujol): 3300 cm$^{-1}$.

NMR (CDCl$_3$, δ): 1.06 (3H, t, J=7.3Hz), 2.04 (2H, broad s), 2.36 (2H, q, J=7.3Hz), 2.49 (2H, t, J=5.8Hz), 2.89 (2H, broad s), 3.87 (2H, d, J=5.8Hz), 4.28 (1H, broad s), 5.41 (1H, s), 6.54 (1H, J=5.8Hz, broad t), 7.19-7.54 (10H, m).

Mass: 350 (M+), 335, 183.

EXAMPLE 67

N-(4-Pyridylmethyl)-2-hydroxy-2,2-diphenylacetamide hydrochloride mp: 233-235° C.

IR (Nujol): 3320, 3250, 2400, 1660, 1640, 1610 cm$^{-1}$.

NMR (DMSO-d$_6$, δ): 4.56 (2H, d, J=6.1Hz), 7.01 (1H, broad s), 7.22-7.53 (11H, m), 7.81 (2H, d, J=6.5Hz), 8.82 (2H, d, J=6.5Hz), 9.12 (1H, t, J=6.1Hz).

Mass: 211, 183.

EXAMPLE 68

A solution of methylmagnesium bromide (10.23 m mol) in diethyl ether (3.5 ml) and tetrahydrofuran (5 ml) were added to a solution of N-(4-dimethylamino-2-butynyl)-benzoylformamide (0.50 g) in toluene (8 ml) at room temperature. After being heated at 70° C. for 1.5 hours, the mixture was treated with 1N aqueous solution of sodium hydroxide and extracted with ethyl acetate. The extract was washed with brine, dried over magnesium sulfate and evaporated in vacuo. The residue was purified by column chromatography on silica gel with a mixture of chloroform and methanol (15:1) as an eluent to give N-[4-dimethylamino-2-butynyl)-2-hydroxy-2-methyl-2-phenyl-acetamide (0.21 g).

IR (film): 3400, 1660, 1600 cm$^{-1}$.

NMR (CDCl$_3$, δ): 1.40-1.88 (1H, broad m), 1.83 (3H, s), 2.24 (6H, s), 3.18 (2H, s), 3.89-4.19 (2H, m), 6.63-6.87 (1H, broad m), 7.21-7.43 (3H, m), 7.48-7.64 (2H, m).

Mass: 260 (M+), 242.

EXAMPLE 69

A solution of 1-chloroethyl chloroformate (0.53 ml) in methylene chloride (5 ml) was added dropwise to a solution of N-(1-benzyl-1,2,3,6-tetrahydropyridin-4-yl)-methyl-2-cyclohexyl-2-hydroxy-2-phenylacetamide (1.50 g) in methylene chloride (25 ml) below 7° C. After being refluxed for 1 hour, the reaction mixture was evaporated in vacuo. To the residue was added methanol (20 ml) and the mixture was refluxed for 1.5 hours. The reaction mixture was evaporated in vacuo, and to the residue was added 1N aqueous solution of sodium hydroxide. The mixture was extracted with ethyl acetate. The extract was washed with brine, dried over magnesium sulfate and evaporated in vacuo. The residue was recrystallized from a mixture of 2-propanol and ethanol to give N-(1,2,3,6-tetrahydropyridin-4-yl)methyl-2-cyclohexyl-2-hydroxy-2-phenylacetamide (0.19 g).

NMR (DMSO-d$_6$, δ): 0.93-1.79 (10H, m), 1.98-2.14 (2H, broad m), 2.19-2.38 (1H, m), 3.06 (2H, t, J=6.0Hz), 3.43 (2H, s), 3.46-3.76 (2H, m), 5.28 (1H, s), 5.56 (1H, s), 7.17-7.42 (3H, m), 7.53-7.71 (2H, m), 7.97 (1H, t, J=5.9Hz), 8.80-9.09 (1H, broad m).

Mass: 328 (M ), 216, 189.

EXAMPLE 70

A mixture of 2-allyl-2,2-diphenylacetic acid (0.92 g) and thionyl chloride (0.67 g), in benzene (2 ml) was refluxed for an hour. After being cooled, excess thionyl chloride was removed under reduced pressure and co-evaporated with benzene several times. The residue was dissolved in methylene chloride (10 ml) and the solution was treated with a solution of 4-dimethylamino-2-butynylamine (0.49 g) in methylene chloride (5 ml) at 4 to 7° C. After being stirred for 24 hours at room temperature, the solution was poured into water (20 ml) and extracted with methylene chloride, washed with 1N aqueous solution of sodium hydroxide, brine, dried over sodium sulfate and evaporated under reduced pressure. The residual solid was recrystallized from diisopropyl ether to give N-(4-dimethylamino-2-butynyl)-2-allyl-2,2-diphenylacetamide (0.84 g).

mp: 107-109° C.

IR (Nujol): 3320, 1645 cm$^{-1}$.

NMR (CDCl$_3$, δ): 2.22 (6H, s), 3.12-3.30 (4H, m), 4.05 (2H, dt, J=5Hz and 2Hz), 4.90-5.12 (2H, m), 5.64-5.93 (2H, m), 7.18-7.45 (10H, m).

EXAMPLE 71

To a solution of N-(4-dimethylamino-2-butynyl)-2-allyl-2,2-diphenylacetamide (0.70 g) in chloroform (5ml) was added methanolic hydrogen chloride (0.15 g/ml, 0.4 ml) and the solution was evaporated in vacuo. The residue was crystallized from a mixture of diethyl ether and ethyl acetate and recrystallized from ethanol to give  N-(4-dimethylamino-2-butynyl)-2-allyl-2,2-diphenylacetamide hydrochloride (0.65 g).

mp: 199-201° C.

IR (Nujol): 3220, 2750-2100, 1655 cm$^{-1}$.

NMR (DMSO-d$_6$, δ): 2.69 (6H, s), 3.08-3.20 (2H, m), 3.34 (2H, s), 3.85-4.00 (2H, m), 4.83-5.00 (2H, m), 5.40-5.70 (1H, m), 7.16-7.20 (10H, m), 7.92 (1H, t, J=5.5Hz), 10.94 (1H, broad s).

EXAMPLE 72

To a solution of 4,4-diphenyl-5-oxo-2-trifluoromethyl-4,5-dihydroxazole (0.75 g) in acetonitrile (2.5 ml) 4-diethylamino-2-butynylamine (0.45 g) was added and stirred for an hour at room temperature. The solvent was removed under reduced pressure and the residue was purified by column chromatography on silica gel with a mixture of chloroform and methanol as an eluent to give N-(4-diethylamino-2-butynyl)-2-(2,2,2-trifluoroacetylamino)-2,2-diphenylacetamide (0.69 g).

IR (Neat): 3330, 1735, 1680 cm$^{-1}$.

NMR (CDCl$^3$, δ): 1.03 (6H, t, J=8Hz), 2.45 (4H, q, J=8Hz), 3.33 (2H, t, J=2Hz), 3.95-4.10 (2H, m), 5.60 (1H, broad s), 7.23-7.46 (10H, m), 8.63 (1H, broad s).

EXAMPLE 73

A mixture of N-(4-diethylamino-2-butynyl)-2-(2,2,2-trifluoroacetylamino)-2,2-diphenylacetamide (0.11 g) in acetone (2 ml) and 6N hydrochloric acid (1.0 ml) was refluxed for 24 hours. After being cooled, the solvent was evaporated in vacuo. The resulting solution was adjusted to pH 12 with aqueous solution of sodium hydroxide and the separated oil was extracted with ethyl acetate. The extract was washed with brine, dried over sodium sulfate and evaporated in vacuo. The residue was purified by column chromatography on silica gel with a mixture of chloroform and methanol as an eluent to give N-(4-diethylamino-2-butynyl)-2-amino-2,2-diphenylacetamide (0.05 g).

IR (CHCl$_3$): 3430, 3390, 1670 cm$^{-1}$.

NMR (CDC$_3$, δ): 1.03 (6H, t, J=8Hz), 2.26 (2H, s), 2.50 (4H, q, J=8Hz), 3.35 (2H, t, J=2Hz), 4.02 (2H, dt, J=5Hz and 2Hz), 7.10-7.46 (11H, m).

The following compounds (Examples 74 to 92) were obtained according to a similar manner to that of Example 19.

EXAMPLE 74

N-(4-Dimethylamino-2-butynyl)-2-cyclopentyl-2-hydroxy-2-phenylacetamide hydrochloride mp: 154–155° C.

IR (Nujol): 3430, 3310, 2400, 1650 cm$^{-1}$.

NMR (DMSO-d$_6$, δ): 1.10–1.65 (8H, m), 2.64 (6H, s), 2.97 (1H, m), 3.89 (2H, d, J=5.5Hz), 3.97 (2H, s), 5.65 (1H, s), 7.15–7.38 (3H, m), 7.50–7.64 (2H, m), 8.35 (1H, t, J=5.5Hz), 10.84 (1H, s).

Mass: 314, 175.

EXAMPLE 75

N-(4-Dimethylamino-2-butynyl)-2-cycloheptyl-2-hydroxy-2-phenylacetamide hydrochloride mp: 195–196° C.

IR (Nujol): 3400, 3300, 2400, 1640 cm$^{-1}$. NMR (DMSO-d$_6$, δ): 1.06–1.74 (12H, m), 2.42–2.69 (1H, m), 2.64 (6H, s), 3.88 (2H, d, J=5.6Hz), 3.96 (2H, s), 5.56 (1H, s), 7.15–7.38 (3H, m), 7.52–7.64 (2H, m), 8.33 (1H, t, J=5.6Hz), 10.55 (1H, broad s).

Mass: 342, 203.

EXAMPLE 76

N-[4-(N-Methylethylamino)-2-butynyl]-2-cyclohexyl-2-hydroxy-2-phenylacetamide hydrochloride mp: 144–145° C.

IR (Nujol): 3350, 2350, 1640 cm$^{-1}$.

NMR (DMSO-d$_6$, δ): 0.87–1.79 (10H, m), 1.14 (3H, t, J=7.2Hz), 2.21–2.39 (1H, m), 2.62 (3H, s), 2.89–3.10 (2H, m), 3.85–3.94 (2H, m), 3.98 (2H, s), 5.55 (1H, s), 7.19–7.39 (3H, m), 7.56 (2H, d, J=8.3Hz), 8.32 (1H, t, J=5.9Hz), 9.95–10.09 (1H, broad m).

Mass: 342, 327, 266, 189.

EXAMPLE 77

N-[2-(Diethylamino)ethyl]-2-cyclohexyl-2-hydroxy-2-phenylacetamide hydrochloride mp: 184–187° C.

IR (Nujol): 3300, 2550, 1640 cm$^{-1}$.

NMR (DMSO-d$_6$, δ): 0.73–1.96 (16H, m), 2.00–2.40 (1H, m), 2.73–3.17 (6H, m), 3.17–3.57 (2H, m), 5.53 (1H, s), 7.07–7.40 (3H, m), 7.47–7.63 (2H, m), 8.23 (1H, t, J=6Hz), 10.53 (1H, broad s).

Mass: 332, 303, 260, 189.

EXAMPLE 78

N-(1-Ethylpiperidin-4-yl)methyl-2-cyclohexyl-2-hydroxy-2-phenylacetamide hydrochloride mp: 222–223° C.

IR (Nujol): 3400, 3250, 2650, 2600, 2400, 1640 cm$^{-1}$.

NMR (DMSO-d$_6$, δ): 0.85–1.84 (15H, m), 1.20 (3H, t, J=7.2Hz), 2.12–2.35 (1H, m), 2.58–3.15 (6H, m), 3.27–3.49 (2H, m), 5.48 (1H, s), 7.13–7.38 (3H, m), 7.53–7.65 (2H, m), 7.90–8.05 (1H, m), 9.75 (1H, broad s).

Mass: 358, 343, 329, 275, 189.

EXAMPLE 79

N-(1,2,3,6-Tetrahydropyridin-4-yl)methyl-2-cyclohexyl-2-hydroxy-2-phenylacetamide hydrochloride mp: 238–240° C.

IR (Nujol): 3330, 2670, 2570, 2480, 1650, 1590 cm$^{-1}$.

NMR (DMSO-d$_6$, δ): 0.91–1.80 (10H, m), 2.00–2.13 (2H, broad s), 2.20–2.40 (1H, broad s), 3.06 (2H, t, J=5.9Hz), 3.44 (2H, s), 3.50–3.77 (2H, m), 5.28 (1H, s), 5.56 (1H, s), 7.18–7.41 (3H, m), 7.53–7.64 (2H, m), 7.98 (1H, t, J=6.4Hz), 8.95 (2H, s).

Mass: 328, 309, 216, 189.

EXAMPLE 80

N-(1-Methyl-1,2,3,6-tetrahydropyridin-4-yl)methyl-2-cyclohexyl-2-hydroxy-2-phenylacetamide hydrochloride mp: 189–190° C.

IR (Nujol): 3460, 3350, 3270, 2670, 2600, 1640 cm$^{-1}$.

NMR (DMSO-d$_6$, δ): 0.84–1.83 (10H, m), 2.01–2.37 (3H, m), 2.71 (3H, s), 2.90–3.41 (2H, broad s), 3.43–3.78 (4H, m), 5.24 (1H, s), 5.58 (1H, s), 7.10–7.40 (3H, m), 7.48–7.65 (2H, m), 8.02 (1H, t, J=5.9Hz), 10.57 (1H, broad s).

Mass: 342, 189.

EXAMPLE 81

N-(1-Ethyl-1,2,3,6-tetrahydropyridin-4-yl)methyl-2-cyclohexyl-2-hydroxy-2-phenylacetamide hydrochloride mp: 170–172° C.

IR (Nujol): 3400, 2480, 1660 cm$^{-1}$.

NMR (DMSO-d$_6$, δ): 0.87–1.94 (10H, m), 1.20 (3H, t, J=7Hz), 1.94–2.44 (3H, m), 2.73–3.87 (8H, m), 5.27 (1H, m), 5.50 (1H, s), 7.13–7.45 (3H, m), 7.45–7.76 (2H, m), 7.95 (1H, t, J=5Hz), 10.00–10.40 (1H, broad s).

Mass: 356, 189.

EXAMPLE 82

N-(1-Benzyl-1,2,3,6-tetrahydropyridin-4-yl)methyl-2-cyclohexyl-2-hydroxy-2-phenylacetamide hydrochloride mp: 133–136° C.

IR (Nujol): 3300, 2570, 1650 cm$^{-1}$.

NMR (DMSO-d$_6$, δ): 0.78–1.61 (10H, m), 1.73–2.17 (3H, m), 2.47–3.37 (6H, m), 4.28 (2H, s), 5.24 (1H, broad s), 5.55 (1H, s), 6.29–6.75 (10H, m), 8.00 (1H, s), 10.42 (1H, s).

Mass: 418, 327, 282, 189, 172, 91.

EXAMPLE 83

N-(1-Ethyl-1,2,3,6-tetrahydropyridin-4-yl)methyl-2-chloro-2-cyclohexyl-2-phenylacetamide hydrochloride mp: 149–150° C.

IR (Nujol): 3480, 3370, 2500, 1660 cm$^{-1}$.

NMR (DMSO-d$_6$, δ): 0.77–1.90 (10H, m), 1.22 (3H, t, J=7Hz), 1.90–2.40 (2H, m), 2.40–2.80 (1H, m), 2.80–3.80 (6H, m), 3.04 (2H, q, J=7Hz), 5.23 (1H, s), 7.23–7.70 (5H, m), 8.33 (1H, t, J=5Hz), 10.73 (1H, broad s).

EXAMPLE 84

N-(4-Cyclopropylamino-2-butynyl)-2-hydroxy-2,2-diphenylacetamide hydrochloride mp: 135–136° C.

IR (Nujol): 3350, 2410, 1670 cm$^{-1}$.

NMR (DMSO-d$_6$, δ): 0.58–0.76 (2H, m), 0.76–0.92 (2H, m), 2.56–2.73 (1H, m), 3.92 (2H, s), 4.01 (2H, d, J=5.7Hz), 6.81 (1H, s), 7.18–7.44 (10H, m), 8.61 (1H, t, J=5.7Hz), 9.53 (2H, s).

Mass: 333, 319, 316, 183.

EXAMPLE 85

N-[4-(N-Methylethylamino)-2-butynyl]-2-hydroxy-2,2-diphenylacetamide hydrochloride mp: 176–177° C.

IR (Nujol): 3340, 3250, 2450, 1670, 1600 cm$^{-1}$.

NMR (DMSO-d$_6$, δ): 1.17 (3H, t, J=7.2Hz), 2.65 (3H, s), 3.03 (2H, q, J=7.2Hz), 4.01 (2H, d, J=5Hz), 4.02 (2H, s), 6.81 (1H, s), 7.28–7.39 (10H, m), 8.69 (1H, t, J=5Hz), 10.74 (1H, s).

Mass: 336, 321, 183.

EXAMPLE 86

N-[4-(N-Methyl-2-hydroxyethylamino)-2-butynyl]-2-hydroxy-2,2-diphenylacetamide hydrochloride mp: 163–164° C.

IR (Nujol): 3320, 1650 cm$^{-1}$.

NMR (DMSO-d$_6$, δ): 2.71 (3H, s), 3.11 (2H, broad s), 3.69 (2H, broad s), 4.00 (2H, d, J=5.3Hz), 4.06 (2H, s), 5.28–5.43 (1H, broad m), 6.82 (1H, s), 7.20–7.45 (10H, m), 8.69 (1H, t, J=5.3Hz), 10.30 (1H, broad s).

Mass: 352, 321, 260, 183.

EXAMPLE 87

N-(4-Dimethylamino-2-butynyl)-2-hydroxy-2,2-bis(2-chlorophenyl)acetamide hydrochloride mp: 167–168° C.

IR (Nujol): 3270, 1680 cm$^{-1}$.

NMR (DMSO-d$_6$, δ): 2.72 (6H, s), 4.05 (4H, s), 6.72 (1H, s), 7.25–7.49 (8H, m), 8.59–8.72 (1H, broad m), 10.84 (1H, broad s).

Mass: 394, 392, 390, 251.

EXAMPLE 88

N-(4-Dimethylamino-2-butynyl)-2-hydroxy-2,2-4-methoxyphenyl)acetamide hydrochloride mp: 160–161° C. (decomposed).

IR (Nujol): 3400, 2400, 1680, 1600 cm$^{-1}$.

NMR (DMSO-d$_6$, δ): 2.65 (6H, s), 3.75 (6H, s), 3.98 (4H, m), 6.90 (4H, d, J=8.9Hz), 7.24 (4H, d, J=8.9Hz), 8.68 (1H, m), 10.48 (1H, m),

Mass: 364, 320, 285, 257, 243.

EXAMPLE 89

N-(1-Ethyl-1,2,3,6-tetrahydropyridin-4-yl)methyl-2-hydroxy-2,2-diphenylacetamide hydrochloride mp: 179–180° C.

IR (Nujol): 3310, 3230, 2550, 1660 cm$^{-1}$.

NMR (DMSO-d$_6$, δ): 1.23 (3H, t, J=7.2Hz), 2.06–2.24 (2H, m), 3.07 (2H, q, J=7.2Hz), 3.26–3.81 (4H, m), 3.73 (2H, d, J=6.0Hz), 5.39 (1H, broad s), 6.81 (1H, broad s), 7.20–7.44 (10H, m), 8.37 (1H, t, J=6.0Hz).

Mass: 350, 335, 302, 183.

EXAMPLE 90

N-(4-Dimethylamino-2-butynyl)-9-xanthenecarboxamide hydrochloride mp: 211–212° C.

IR (Nujol): 3400, 3250, 2430, 1640, 1620 cm$^{-1}$.

NMR (DMSO-d$_6$, δ): 2.67 (6H, s), 3.96 (2H, d, J=5.4Hz), 4.01 (2H, s), 5.00 (1H, s), 7.04–7.22 (4H, m), 7.24–7.38 (4H, m), 9.11 (1H, t, J=5.4Hz), 10.75 (1H, s).

Mass: 320, 181.

EXAMPLE 91

N-(4-Diethylamino-2-butynyl)-2-(2,2,2-trifluoroacetylamino)-2,2-diphenylacetamide hydrochloride IR (CHCl$_3$): 3420, 3340, 2600–2000, 1730, 1680 cm$^{-1}$.

NMR (CDCl$_3$, δ): 1.38 (6H, t, J=8Hz), 2.70–3.23 (4H, m), 3.70–3.86 (2H, m), 3.96–4.16 (2H, m), 6.20 (1H, broad s), 7.33 (10H, s), 8.43 (1H, broad s).

EXAMPLE 92

N-(4-Diethylamino-2-butynyl)-2-amino-2,2-diphenylacetamide bis(hydrochloride)

IR (KBr): 3000–2200, 1680, 1670 cm$^{-1}$.

NMR (DMSO-d$_6$, δ): 1.26 (6H, t, J=7Hz), 2.90–3.40 (4H, m), 3.90–4.20 (4H, m), 7.20–7.60 (10H, m), 8.40 (1H, broad s), 9.43 (3H, broad s).

The following compounds (Examples 93 to 115) were obtained according to a similar manner to that of Example 1.

EXAMPLE 93

N-(4-Diethylamino-2-butynyl)-2-chloro-2-cyclohexyl-2-phenylacetamide hydrochloride IR (Nujol): 3280, 2470, 2420, 1665 cm$^{-1}$.

EXAMPLE 94

N-(4-Diethylamino-2-butynyl)-2-cyclohexyl-2-hydroxy-2-phenylacetamide

IR (Nujol): 3400, 1665 cm$^{-1}$.

EXAMPLE 95

N-[2-(Diethylamino)ethyl]-2-chloro-2-cyclohexyl-2-phenylacetamide

IR (film): 3380, 1660 cm$^{-1}$.

EXAMPLE 96

N-(1-Ethyl-1,2,3,6-tetrahydropyridin-4-yl)methyl-2-chloro-2-cyclohexyl-2-phenylacetamide IR (film): 3440, 3370, 1670, 1600 cm$^{-1}$.

EXAMPLE 97

N-(4-Dimethylamino-2-butynyl)-2-chloro-2,2-bis(2-chlorophenyl)acetamide

IR (CHCl$_3$) 3430, 3350, 1670 cm$^{-1}$.

EXAMPLE 98

N-(4-Dimethylamino-2-butynyl)-2-hydroxy-2,2-bis(4-methoxyphenyl)acetamide

IR (CHCl ): 3410, 2050, 1670, 1610 cm$^{-1}$.

EXAMPLE 99

N-(4-Dimethylamino-2-butynyl)-9-xanthenecarboxamide

IR (Nujol): 3300, 1640 cm$^{-1}$.

EXAMPLE 100

N-[2-(Diethylamino)ethyl]-2-cyclohexyl-2-hydroxy-2-phenylacetamide

IR (Nujol): 3360, 1660 cm$^{-1}$.

EXAMPLE 101

N-(1-Ethyl-1,2,3,6-tetrahydropyridin-4-yl)methyl-2-cyclohexyl-2-hydroxy-2-phenylacetamide IR (film): 3400, 1660, 1600 cm$^{-1}$.

EXAMPLE 102

N-(4-Dimethylamino-2-butynyl)-2-hydroxy-2,2-bis(2-chlorophenyl)acetamide

IR (CHCl$_3$): 3550, 3400, 1680 cm$^{-1}$.

EXAMPLE 103

N-(4-Dimethylamino-2-butynyl)-2-cyclopentyl-2-hydroxy-2-phenylacetamide

IR (film): 3400, 1650, 1600 cm$^{-1}$.

EXAMPLE 104

N-(4-Dimethylamino-2-butynyl)-2-cycloheptyl-2-hydroxy-2-phenylacetamide
IR (Nujol): 3310, 1660 cm$^{-1}$.

EXAMPLE 105

N-(1-Methyl-1,2,3,6-tetrahydropyridin-4-yl)methyl-2-cyclohexyl-2-hydroxy-2-phenylacetamide
IR (Nujol): 3300, 3050, 1660, 1600 cm$^{-1}$.

EXAMPLE 106

N-(1-Ethylpiperidin-4-yl)methyl-2-cyclohexyl-2-hydroxy-2-phenylacetamide
IR (Nujol): 3400, 3300, 1650 cm$^{-1}$.

EXAMPLE 107

N-(1-Benzyl-1,2,3,6-tetrahydropyridin-4-yl)methyl-2-cyclohexyl-2-hydroxy-2-phenylacetamide
IR (Nujol): 3410, 3270, 1660, 1600 cm$^{-1}$.

EXAMPLE 108

N-(4-Dimethylamino-2-butynyl)-2-hydroxy-2,2-4-methylphenyl)acetamide
IR (CHCl$_3$) 3400, 1660, 1610 cm$^{-1}$.

EXAMPLE 109

N-(1-Ethyl-1,2,3,6-tetrahydropyridin-4-yl)methyl-2-hydroxy-2,2-diphenylacetamide
IR (Nujol): 3300 cm$^{-1}$.

EXAMPLE 110

N-(4-Pyridylmethyl)-2-hydroxy-2,2-diphenylacetamide hydrochloride
IR (Nujol): 3320, 3250, 2400, 1660, 1640, 1610 cm$^{-1}$.

EXAMPLE 111

N-(4-Dimethylamino-2-butynyl)-2-hydroxy-2-methyl-2-phenylacetamide
IR (film): 3400, 1660, 1600 cm$^{-1}$.

EXAMPLE 112

N-(1,2,3,6-Tetrahydropyridin-4-yl)methyl-2-cyclohexyl-2-hydroxy-2-phenylacetamide
Mass: 328 (M+), 216, 189.

EXAMPLE 113

N-(4-Dimethylamino-2-butynyl)-2-allyl-2,2-diphenylacetamide
IR (Nujol): 3320, 1645 cm$^{-1}$.

EXAMPLE 114

N-(4-Diethylamino-2-butynyl)-2-(2,2,2-trifluoroacetylamino)-2,2-diphenylacetamide
IR (Neat): 3330, 1735, 1680 cm$^{-1}$.

EXAMPLE 115

N-(4-Diethylamino-2-butynyl)-2-amino-2,2-diphenylacetamide
IR (CHCl$_3$) 3430, 3390, 1670 cm$^{-1}$.

The following compounds (Examples 116 to 149) were obtained according to a similar manner to that of Example 43.

EXAMPLE 116

N-(4-Dimethylamino-2-butynyl)-2-cyclohexyl-2-hydroxy-2-phenylacetamide
IR (CHCl$_3$) 3400, 1650 cm$^{-1}$.

EXAMPLE 117

N-(4-Methylamino-2-butynyl)-2-cyclohexyl-2-hydroxy-2phenylacetamide
IR (CHCl$_3$): 3400, 1660 cm$^{-1}$.

EXAMPLE 118

N-(4-Ethylamino-2-butynyl)-2-cyclohexyl-2-hydroxy-2-phenylacetamide
IR (film): 3400, 1650 cm$^{-1}$.

EXAMPLE 119

N-(4-Butylamino-2-butynyl)-2-cyclohexyl-2-hydroxy-2-phenylacetamide
IR (film): 3400, 1600 cm$^{-1}$.

EXAMPLE 120

N-(4-t-Butylamino-2-butynyl)-2-cyclohexyl-2-hydroxy-2-phenylacetamide
IR (CHCl$_3$) 3400, 1650 cm$^{-1}$.

EXAMPLE 121

N-(4-Cyclohexylamino-2-butynyl)-2-cyclohexyl-2-hydroxy-2-phenylacetamide
IR (CHCl$_3$) 3400, 1600 cm$^{-1}$.

EXAMPLE 122

N-[4-(2-Hydroxyethyl)amino-2-butynyl]-2-cyclohexyl-2-hydroxy-2-phenylacetamide
IR (CHCl$_3$) 3400, 1650 cm$^{-1}$.

EXAMPLE 123

N-[4-(Ethoxycarbonylmethyl)amino-2-butynyl]-2-cyclohexyl-2-hydroxy-2-phenylacetamide
IR (film): 3380, 1730, 1660 cm$^{-1}$.

EXAMPLE 124

N-[4-(N-Methyl)phenylamino-2-butynyl]-2-cyclohexyl-2-hydroxy-2-phenylacetamide
IR (CHCl$_3$): 3400, 1600 cm$^{-1}$.

EXAMPLE 125

N-[4-(N-Ethyl)benzylamino-2-butynyl]-2-cyclohexyl-2-hydroxy-2-phenylacetamide
IR (film): 3400, 1650 cm$^{-1}$.

EXAMPLE 126

N-[4-{2-(3,4-Dimethoxyphenyl)ethylamino}-2-butynyl]-2-cyclohexyl-2-hydroxy-2-phenylacetamide
IR (film): 3420, 1660 cm$^{-1}$.

EXAMPLE 127

N-[4-{N-Methyl-1-methyl-2-(4-methoxyphenyl)-ethylamino}-2-butynyl]-2-cyclohexyl-2-hydroxy-2-phenylacetamide
IR (film): 3400, 1660 cm$^{-1}$.

EXAMPLE 128

N-(4-Piperidino-2-butynyl)-2-cyclohexyl-2-hydroxy-2-phenylacetamide
IR (CHCl$_3$): 3400, 1660 cm$^{-1}$.

EXAMPLE 129

N-[4-{3-Azabicyclo[3.2.2]nonan-3-yl}-2-butynyl]-2-cyclohexyl -2-hydroxy-2-phenylacetamide
IR (CHCl3) 3400, 1660 cm$^{-1}$.

EXAMPLE 130

N-(4-Morpholino-2-butynyl)-2-cyclohexyl-2-hydroxy-2-phenylacetamide
IR (film): 3400, 1660 cm$^{-1}$.

EXAMPLE 131

N-[4-(4-Methyl-1-piperazinyl)-2-butynyl]-2-cyclohexyl-2-hydroxy-2-phenylacetamide
IR (film): 3400, 1660 cm$^{-1}$.

EXAMPLE 132

N-[4-(4-Hydroxypiperidino)-2-butynyl]-2-cyclohexyl-2-hydroxy-2-phenylacetamide
NMR (CDCl$_3$, δ): 0.60–2.93 (21H, m), 3.20 (2H, m), 3.50–3.86 (1H, m), 3.86–4.09 (2H, m), 6.70–7.03 (1H, m), 7.10–7.45 (3H, m), 7.45–7.73 (2H, m).

EXAMPLE 133

N-[4-(2-Hydroxymethylpiperidino)-2-butynyl]-2-cyclohexyl-2-hydroxy-2-phenylacetamide
IR (CHCl$_3$) 3400, 1660 cm$^{-1}$.

134

N-[4-{2-(Cyanoimino)-1-imidazolidinyl}-2-butynyl]-2-cyclohexyl-2-hydroxy-2-phenylacetamide
IR (Nujol): 3300, 2170, 1650 cm$^{-1}$.

EXAMPLE 135

N-(4-Dimethylamino-2-butynyl)-2-hydroxy-2,2-diphenylacetamide
IR (CHCl$_3$) 3400, 1660 cm$^{-1}$.

EXAMPLE 136

N-(4-Methylamino-2-butynyl)-2-hydroxy-2,2-diphenylacetamide
IR (CHCl$_3$) 3400, 3300, 1660 cm$^{-1}$.

EXAMPLE 137

N-(4-Diethylamino-2-butynyl)-2-cyclohexyl-2-hydroxy-2-phenylacetamide
IR (Nujol): 3400, 1665 cm$^{-1}$.

EXAMPLE 138

N-[4-(N-Methylethylamino)-2-butynyl]-2-cyclohexyl-2-hydroxy-2-phenylacetamide
IR (film): 3400, 3070, 1660 cm$^{-1}$.

EXAMPLE 139

N-(4-Propylamino-2-butynyl)-2-hydroxy-2,2-diphenylacetamide
IR (Nujol): 3370, 3280, 1660 cm$^{-1}$.

EXAMPLE 140

N-(4-Cyclopropylamino-2-butynyl-2-hydroxy-2,2-diphenylacetamide
IR (CHCl$_3$): 3400, 3050, 3000, 1660, 1600 cm$^{-1}$.

EXAMPLE 141

N-[4-(N-Methylethylamino)-2-butynyl]-2-hydroxy-2,2-diphenylacetamide
IR (CHCl$_3$) 3400, 1660, 1600 cm$^{-1}$.

EXAMPLE 142

N-[4-(N-Methyl-2-hydroxyethylamino)-2-butynyl]-2-hydroxy-2,2-diphenylacetamide
IR (Nujol): 3350, 3170, 1630 cm$^{-1}$.

EXAMPLE 143

N-[2(Diethylamino)ethyl]-2-cyclohexyl-2-hydroxy-2-phenylacetamide
IR (Nujol): 3360, 1660 cm$^{-1}$.

EXAMPLE 144

N-(1-Ethyl-1,2,3,6-tetrahydropyridin-4-yl)methyl-2-cyclohexyl-2-hydroxy-2-phenylacetamide
IR (film): 3400, 1660, 1600 cm$^{-1}$.

EXAMPLE 145

N-(4-Dimethylamino-2-butynyl)-2-hydroxy-2,2-bis(2-chlorophenyl)acetamide
IR (CHCl$_3$): 3550, 3400, 1680 cm$^{-1}$.

EXAMPLE 146

N-(4-Dimethylamino-2-butynyl)-2-hydroxy-2-methyl-2-phenylacetamide
IR (film): 3400, 1660, 1600 cm$^{-1}$.

EXAMPLE 147

N-(1,2,3,6-Tetrahydropyridin-4-yl)methyl-2-cyclohexyl-2-hydroxy-2-phenylacetamide
Mass: 328 (M+), 216, 189.

EXAMPLE 148

N-(4-Diethylamino-2-butynyl)-2-(2,2,2-trifluoroacetylamino)-2,2-diphenylacetamide
IR (Neat): 3330, 1735, 1680 cm$^{-1}$.

EXAMPLE 149

N-(4-Diethylamino-2-butynyl)-2-amino-2,2-diphenylacetamide
IR (CHCl$_3$): 3430, 3390, 1670 cm$^{-1}$.

The following compounds (Examples 150 to 179) were obtained according to a similar manner to that of Example 57.

EXAMPLE 150.

N-(4-Dimethylamino-2-butynyl)-2-cyclohexyl-2-hydroxy-2-phenylacetamide
IR (CHCl$_3$): 3400, 1650 cm$^{-1}$.

EXAMPLE 151

N-(4-Methylamino-2-butynyl)-2-cyclohexyl-2-hydroxy-2-phenylacetamide
IR (CHCl$_3$): 3400, 1660 cm$^{-1}$.

EXAMPLE 152

N-(4-Ethylamino-2-butynyl)-2-cyclohexyl-2-hydroxy-2-phenylacetamide
IR (film): 3400, 1650 cm$^{-1}$.

EXAMPLE 153

N-(4-Butylamino-2-butynyl)-2-cyclohexyl-2-hydroxy-2-phenylacetamide
IR (film): 3400, 1600 cm$^{-1}$.

EXAMPLE 154

N-(4-t-Butylamino-2-butynyl)-2-cyclohexyl-2-hydroxy-2-phenylacetamide
IR (CHCl$_3$): 3400, 1650 cm$^{-1}$.

EXAMPLE 155

N-(4-Cyclohexylamino-2-butynyl)-2-cyclohexyl-2-hydroxy-2-phenylacetamide
IR (CHCl$_3$) 3400, 1600 cm$^{-1}$.

EXAMPLE 156

N-[4-(2-Hydroxyethyl)amino-2-butynyl]-2-cyclohexyl-2-hydroxy-2-phenylacetamide
IR (CHCl$_3$): 3400, 1650 cm$^{-1}$.

EXAMPLE 157

N-[4-(Ethoxycarbonylmethyl)amino-2-butynyl]-2-cyclohexyl-2-hydroxy-2-phenylacetamide
IR (film): 3380, 1730, 1660 cm$^{-1}$.

EXAMPLE 158

N-[4-(N-Methyl)phenylamino-2-butynyl]-2-cyclohexyl-2-hydroxy-2-phenylacetamide
IR (CHCl$_3$) 3400, 1600 cm$^{-1}$.

EXAMPLE 159

N-[4-(N-Ethyl)benzylamino-2-butynyl]-2-cyclohexyl-2-hydroxy-2-phenylacetamide
IR (film): 3400, 1650 cm$^{-1}$.

EXAMPLE 160

N-[4-{2-(3,4-Dimethoxyphenyl)ethylamino}-2-butynyl]-2-cyclohexyl-2-hydroxy-2-phenylacetamide
IR (film): 3420, 1660 cm$^{-1}$.

EXAMPLE 161

N-[4-{N-Methyl-1-methyl-2-(4-methoxyphenyl)ethylamino}-2-butynyl]-2-cyclohexyl-2-hydroxy-2-phenyl-acetamide
IR (film): 3400, 1660 cm$^{-1}$.

EXAMPLE 162

N-(4-Piperidino-2-butynyl)-2-cyclohexyl-2-hydroxy-2-phenylacetamide
IR (CHCl$_3$): 3400, 1660 cm$^{-1}$.

EXAMPLE 163

N-[4-{3-Azabicyclo[3.2.2]nonan-3-yl}-2-butynyl]-2-cyclohexyl-2-hydroxy-2-phenylacetamide
IR (CHCl$_3$): 3400, 1660 cm$^{-1}$.

EXAMPLE 164

N-(4-Morpholino-2-butynyl)-2-cyclohexyl-2-hydroxy-2-phenylacetamide
IR (film): 3400, 1660 cm$^{-1}$.

EXAMPLE 165

N-[4-(4-Methyl-1-piperazinyl)-2-butynyl]-2-cyclohexyl-2-hydroxy-2-phenylacetamide
IR (film): 3400, 1660 cm$^{-1}$.

EXAMPLE 166

N-[4-(4-Hydroxypiperidino)-2-butynyl]-2-cyclohexyl-2-hydroxy-2-phenylacetamide
NMR (CDCl$_3$, $\delta$): 0.60–2.93 (21H, m), 3.20 (2H, m), 3.50–3.86 (1H, m), 3.86–4.09 (2H, m), 6.70–7.03 (1H, m), 7.10–7.45 (3H, m), 7.45–7.73 (2H, m),

EXAMPLE 167

N-[4-(2-Hydroxymethylpiperidino)-2-butynyl]-2-cyclohexyl-2-hydroxy-2-phenylacetamide
IR (CHCl$_3$) 3400, 1660 cm$^{-1}$.

EXAMPLE 168

N-[4-{2-(Cyanoimino)-1-imidazolidinyl}-2-butynyl]-2-cyclohexyl-2-hydroxy-2-phenylacetamide
IR (Nujol): 3300, 2170, 1650 cm$^{-1}$.

EXAMPLE 169

N-(4-Dimethylamino-2-butynyl)-2-hydroxy-2,2-diphenylacetamide
IR (CHCl$_3$) 3400, 1660 cm$^{-1}$.

EXAMPLE 170

N-(4-Methylamino-2-butynyl)-2-hydroxy-2,2-diphenylacetamide
IR (CHCl$_3$): 3400, 3300, 1660 cm$^{-1}$.

EXAMPLE 171

N-[4-(N-Methylethylamino)-2-butynyl]-2-cyclohexyl-2-hydroxy-2-phenylacetamide
IR (film): 3400, 3070, 1660 cm$^{-1}$.

EXAMPLE 172

N-(4-Propylamino-2-butynyl)-2-hydroxy-2,2-diphenylacetamide
IR (Nujol): 3370, 3280, 1660 cm$^{-1}$.

EXAMPLE 173

N-(4-Cyclopropylamino-2-butynyl)-2-hydroxy-2,2-diphenylacetamide
IR (CHCl$_3$): 3400, 3050, 3000, 1660, 1600 cm$^{-1}$.

EXAMPLE 174

N-[4-(N-Methylethylamino)-2-butynyl]-2-hydroxy-2,2-diphenylacetamide
IR (CHCl$_3$): 3400, 1660, 1600 cm$^{-1}$.

EXAMPLE 175

N-[4-(N-Methyl-2-hydroxyethylamino-2-butynyl]-2-O hydroxy-2,2-diphenylacetamide
IR (Nujol): 3350, 3170, 1630 cm$^{-1}$.

EXAMPLE 176

N-(4-Dimethylamino-2-butynyl)-2-hydroxy-2,2-bis(4-methoxyphenyl)acetamide
IR (CHCl$_3$): 3410, 2050, 1670, 1610 cm$^{-1}$.

EXAMPLE 177

N-(4-Dimethylamino-2-butynyl)-2-hydroxy-2-methyl-2-phenylacetamide
IR (film): 3400, 1660, 1600 cm$^{-1}$.

EXAMPLE 178

N-(1,2,3,6-Tetrahydropyridin-4-yl)methyl-2-cyclohexyl-2-hydroxy-2-phenylacetamide
Mass: 328 (M$^+$), 216, 189.

EXAMPLE 179

N-(4-Ethylamino-2-butynyl)-2-hydroxy-2,2-diphenylacetamide hydrochloride
IR (Nujol): 3400, 3300, 3220, 2650, 1650 cm$^{-1}$.

EXAMPLE 180

N-(4-Ethylamino-2-butynyl)-2-hydroxy-2,2-diphenylacetamide hydrochloride was obtained according to a similar manner to that of Example 43.
IR (Nujol): 3400, 3300, 3220, 2650, 1650 cm$^{-1}$.
What is claimed is:
1. A compound of the formula

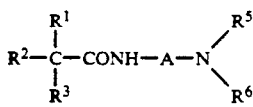

wherein $R^1$ is selected from the group consisting of phenyl and phenyl substituted by 1 to 3 substituents independently selected from the group consisting of halo, lower alkyl and lower alkoxy;

$R^2$ is selected from the group consisting of phenyl; phenyl substituted by 1 to 3 substituents independently selected from the group consisting of halo, lower alkyl and lower alkoxy; and cyclo(lower)alkyl;

$R^3$ is hydroxy;

A is lower alkynylene;

$R^5$ is selected from the group consisting a lower alkyl; hydroxy(lower)alkyl; cyclo(lower)alkyl; phenyl; phenyl(lower)alkyl; and phenyl(lower)alkyl wherein the phenyl ring is substituted by 1 to 3 lower alkoxy substituents; and $R^6$ is hydrogen or lower alkyl;

or a pharmaceutically acceptable salt thereof.

2. A compound of claim 1, wherein
$R^1$ and $R^2$ are each phenyl,
$R^3$ is hydroxy,
$R^4$ is a group of the formula:

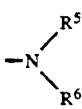

(wherein $R^5$ is lower alkyl, and
$R^6$ is hydrogen or lower alkyl), and
A is lower alkynylene.

3. A compound of claim 2, wherein
$R^4$ is a group of the formula:

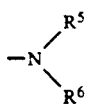

(wherein $R^5$ is ethyl, and
$R^6$ is hydrogen or methyl), and
A is 2-butynylene.

4. A compound of claim 3, which is selected from a compound consisting of: N-(4-ethylamino-2-butynyl)-2-hydroxy-2,2-diphenylacetamide, and N-[4-(N-methylethylamino)-2-butynyl]-2-hydroxy-2,2-diphenylacetamide.

5. A compound of claim 4, which is N-(4-ethylamino-2-butynyl)-2-hydroxy-2,2-diphenylacetamide.

6. A compound of claim 1, wherein
$R^1$ is phenyl,
$R^2$ is cyclo(lower)alkyl,
$R^3$ is hydroxy,
$R^4$ is a group of the formula:

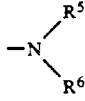

(wherein $R^5$ and $R^6$ are each lower alkyl), and A is lower alkynylene.

7. A compound of claim 6, which is selected from a compound consisting of:
N-(4-dimethylamino-2-butynyl)-2-cyclopentyl-2-hydroxy-2-phenylacetamide, and
N-(4-dimethylamino-2-butynyl)-2-cyclohexyl-2-hydroxy-2-phenylacetamide.

8. A pharmaceutical composition for treatment of dysuria which comprises, as an active ingredient, an effective amount of a compound of claim 1 or a pharmaceutically acceptable salt thereof in admixture with pharmaceutically acceptable carriers.

9. A method for the treatment of dysuria, which comprises administering an effective amount of a compound or pharmaceutically acceptable salt of claim 1 to subjects in need of such treatment.

* * * * *